US010416082B2

(12) United States Patent
Meinhart et al.

(10) Patent No.: US 10,416,082 B2
(45) Date of Patent: *Sep. 17, 2019

(54) DEVICE AND METHODS OF DETECTION OF AIRBORNE AGENTS

(71) Applicants: The Regents of the University of California, Oakland, CA (US); The Board of Trustees of the Leland Stanford Junior University, Palo Alto, CA (US)

(72) Inventors: Carl D. Meinhart, Santa Barbara, CA (US); Brian Piorek, Santa Barbara, CA (US); Seung Joon Lee, Santa Barbara, CA (US); Martin Moskovits, Santa Barbara, CA (US); Sanjoy Banerjee, Santa Barbara, CA (US); Juan Santiago, Stanford, CA (US)

(73) Assignees: The Regents of the University of California, Oakland, CA (US); Board of Trustees of the Leland Stanford Junior University, Palo Alto, CA (US)

( * ) Notice: Subject to any disclaimer, the term of this patent is extended or adjusted under 35 U.S.C. 154(b) by 222 days.

This patent is subject to a terminal disclaimer.

(21) Appl. No.: 15/665,095

(22) Filed: Jul. 31, 2017

(65) Prior Publication Data

US 2018/0024067 A1 Jan. 25, 2018

Related U.S. Application Data

(60) Continuation of application No. 14/814,771, filed on Jul. 31, 2015, now Pat. No. 9,719,930, which is a (Continued)

(51) Int. Cl.
*G01N 21/65* (2006.01)
*G01N 21/05* (2006.01)
(Continued)

(52) U.S. Cl.
CPC .......... *G01N 21/658* (2013.01); *G01N 21/05* (2013.01); *G01N 33/0057* (2013.01);
(Continued)

(58) Field of Classification Search
None
See application file for complete search history.

(56) References Cited

U.S. PATENT DOCUMENTS 6,899,849 B2   5/2005   Meinhart et al.
7,057,198 B2   6/2006   Meinhart et al.
(Continued)

OTHER PUBLICATIONS

Nickitas-Etienne, Athina, International Preliminary Examination Report, The International Bureau of WIPO, PCT/US2008/005345, dated Oct. 27, 2009.

(Continued)

*Primary Examiner* — Xiaoyun R Xu
(74) *Attorney, Agent, or Firm* — Gavrilovich, Dodd & Lindsey LLP

(57) ABSTRACT

Provided are methods, devices and systems that utilize free-surface fluidics and SERS for analyte detection with high sensitivity and specificity. The molecules can be airborne agents, including but not limited to explosives, narcotics, hazardous chemicals, or other chemical species. The free-surface fluidic architecture is created using an open microchannel, and exhibits a large surface to volume ratio. The free-surface fluidic interface can filter interferent molecules, while concentrating airborne analyte molecules. The microchannel flow enables controlled aggregation of SERS-active probe particles in the flow, thereby enhancing the detector's sensitivity.

11 Claims, 12 Drawing Sheets

Related U.S. Application Data continuation of application No. 13/872,778, filed on Apr. 29, 2013, now Pat. No. 9,097,676, which is a continuation of application No. 13/564,698, filed on Aug. 1, 2012, now Pat. No. 8,431,409, which is a continuation of application No. 13/217,616, filed on Aug. 25, 2011, now Pat. No. 8,247,238, which is a division of application No. 12/597,742, filed as application No. PCT/US2008/005345 on Apr. 25, 2008, now Pat. No. 8,017,408.

(60) Provisional application No. 60/914,603, filed on Apr. 27, 2007.

(51) Int. Cl.
*G01N 33/00* (2006.01)
*G01N 21/03* (2006.01)

(52) U.S. Cl.
CPC . *G01N 21/0332* (2013.01); *G01N 2021/0346* (2013.01); *G01N 2201/06113* (2013.01); *G01N 2201/1087* (2013.01); *Y10S 977/902* (2013.01)

(56) References Cited

U.S. PATENT DOCUMENTS

| | | |
|---|---|---|
| 7,087,444 B2 | 8/2006 | Wong et al. |
| 7,283,215 B2 | 10/2007 | Wang et al. |
| 2002/0187074 A1 | 12/2002 | O'Connor et al. |
| 2003/0059820 A1 | 3/2003 | Vo-Dinh |
| 2003/0143580 A1 | 7/2003 | Straus |
| 2003/0226755 A1 | 12/2003 | Ramsey |
| 2005/0036918 A1 | 2/2005 | Lange et al. |
| 2005/0042615 A1 | 2/2005 | Smith et al. |
| 2007/0030481 A1 | 2/2007 | Gilbert |
| 2007/0048746 A1 | 3/2007 | Su et al. |
| 2008/0270042 A1 | 10/2008 | Wu et al. |

OTHER PUBLICATIONS

Piorek, Brian D., "Free-surface microfluidic control of surface-enhanced Raman spectroscopy for the optimized detection of airborne molecules," PNAS, Nov. 27, 2007, vol. 104, No. 48, pp. 18898-18901.

Nickitas-Etienne, Athina, International Preliminary Report on Patentability and Written Opinion, dated Oct. 27, 2009, International Application No. PCT/US08/005345, 8 pages.

Timmer, B. H., et al., "Selective low concentration ammonia sensing in a microfluidic Lab-on-a Chip," 2006, IEEE Sensors Journal, vol. 6(3), pp. 829-835.

Sridharamurthy, S. S., et al., "A microfluidic device to acquire gaseous samples via surface tension held gas-liquid interface," 2007, IEEE Sensors Journal, vol. 7 (9), pp. 1315-1316.

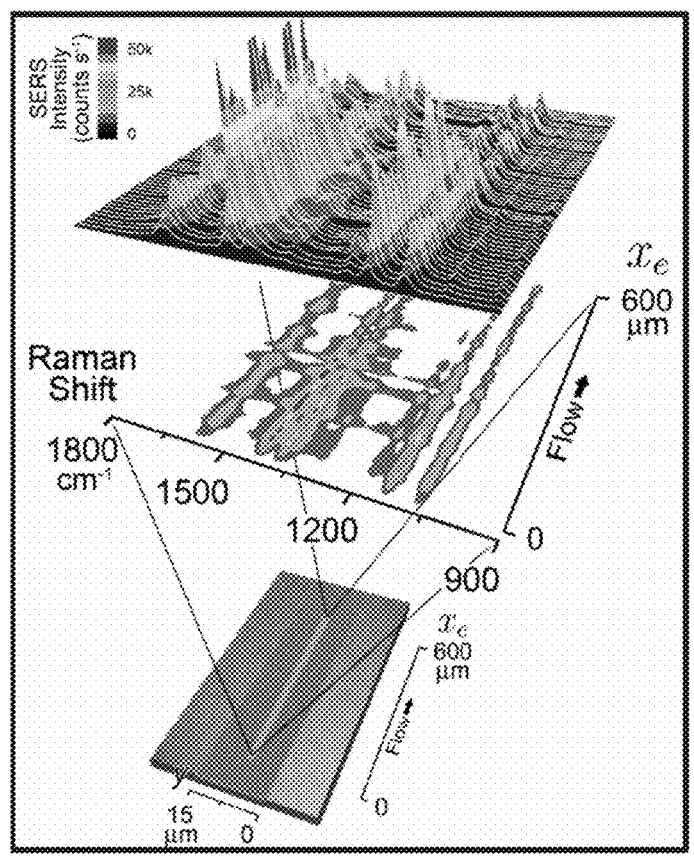
FIG. 16
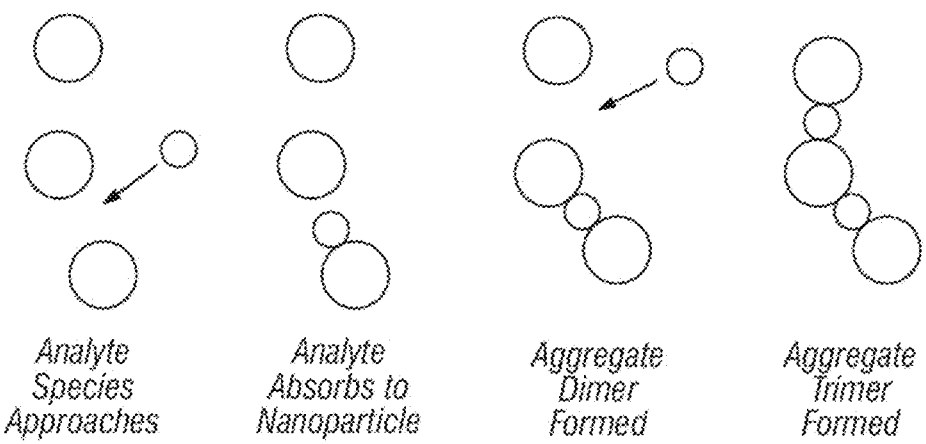
| Analyte | Analyte | Aggregate | Aggregate |
| Species | Absorbs to | Dimer | Trimer |
| Approaches | Nanoparticle | Formed | Formed |
FIG. 17A   FIG. 17B   FIG. 17C   FIG. 17D

DEVICE AND METHODS OF DETECTION OF AIRBORNE AGENTS

CROSS REFERENCE TO RELATED APPLICATIONS

The application is a continuation of U.S. patent application Ser. No. 14/814,771, filed Jul. 31, 2015, which is a continuation of U.S. patent application Ser. No. 13/872,778, filed Apr. 29, 2013, now U.S. Pat. No. 9,097,676, which is a continuation of U.S. patent application Ser. No. 13/564,698, filed Aug. 1, 2012, now U.S. Pat. No. 8,431,409, which is a continuation application and claims priority to U.S. patent application Ser. No. 13/217,616, filed Aug. 25, 2011, now U.S. Pat. No. 8,247,238, which application is a divisional application and claims priority to U.S. patent application Ser. No. 12/597,742, filed Feb. 17, 2010, now U.S. Pat. No. 8,017,408, which is a U.S. National Stage application filed under 35 U.S.C. § 371 and claims priority to International Application No. PCT/US08/005345, filed Apr. 25, 2008, which application claims priority under 35 U.S.C. § 119 to U.S. Provisional Application Ser. No. 60/914,603, filed Apr. 27, 2007, the disclosures of which are incorporated herein by reference.

STATEMENT REGARDING FEDERALLY SPONSORED RESEARCH

This invention was funded in part by Grant No. CTS-9874839 awarded by the National Science Foundation, by Grant No. DAAD19-03-D-0004 awarded by the Army Research Office, and by Grant No. FA9550-04-0106 awarded by the Air Force Office of Scientific Research. The government has certain rights in the invention.

TECHNICAL FIELD

Provided are methods and devices for detecting and measuring airborne agents. In particular, the disclosure provides methods and devices useful for detection of measurements of airborne agents using microfluidics and Raman scattering techniques.

BACKGROUND

Raman spectroscopy is a label-free technique desired for molecular detection and molecular dynamics studies. Surface enhanced Raman scattering (SERS) improves the sensitivity by amplifying the original Raman scattering intensity for several or even tens of orders of magnitude. Spherical gold and silver nanoparticles have been used as substrates in SERS-based molecule detections due to their advantages in local scattering field enhancing, surface chemical modifications, biocompatibility, and well-established chemical synthesis processes. The intrinsic plasmon resonance of single nanoparticles and the plasmon coupling between adjacent nanoparticles are conditions for local field enhancing. The optimal SERS substrate of nanoparticle assemblies depends on the size, the local dielectric environment and the interparticle distance. SERS spectroscopy shows chemical-bond information, and is a useful method for label-free biomolecular imaging.

Nanoparticles are useful, in part, because of their unique, highly desirable properties that makes a superior detection platform for life science research, in vitro diagnostic testing, and in vivo imaging. One such property of nanoparticles is the increased intensity of Raman scattering which they contribute to the measurement of analyte species by Raman spectroscopy. The increased intensity results from the high density of SERS-active sites the nanoparticles contribute to the system. Other structures such as nanotips and nanorings have also been demonstrated for use in high resolution SERS spectroscopy and imaging. These structures provide significant field enhancement in experiments and in simulations.

Microfluidics is a field of work that deals with the fluid-based transport of mass, momentum, or energy. Microfluidic channels are completely enclosed and not in direct communication with the surrounding atmosphere.

SUMMARY

The disclosure provides a microfluidic platform for real time sensing of volatile airborne agents, such as explosives. The system leverages phenomena at multiple length scales, ranging from tens of micrometers to a few nanometers. Free-Surface Fluidics (FSF), are used such that one or more fluid surfaces of a fluid flow channel flow are exposed to the surrounding atmosphere, with confinement being caused by surface tension forces operating, typically, on open-channel flows of order (~100 nm-10 µm) depth. This free-surface fluidic architecture can be incorporated with a variety of sensing techniques for detection of airborne agents. For example, the free-surface fluidic architecture in combination with Surface Enhanced Raman Spectroscopy (SERS) provides useful sensing methods and devices to obtain a sensor that is both sensitive and molecular-specific.

The FSF architecture allows one or more surfaces of the microfluidic flow to be exposed to the atmosphere. Since the length scale is on the order of a few microns, a very large surface area is exposed to the atmosphere. This provides automatic injection of airborne molecules into the microfluidic channel.

The disclosure provides a free-surface detection device comprising: a substrate; a fluid flow channel having a first end and a second end located in or on the substrate; at least one free-surface interface region located between the first end and the second end, wherein the free-surface interface region is open on at least one side to atmospheric air comprising an analyte; an excitation area, wherein electromagnetic energy excites a SERS probe in a fluid flowing in the fluid flow channel containing analytes; and a detection area, wherein an emitted spectra is detected by a detection device, wherein the free-surface interface region is in fluid communication with the excitation and detection areas and wherein analytes in the sample are absorbed into the fluid. The device may further comprise an electromagnetic energy source that emits electromagnetic radiation at the excitation area. The device can further comprise a detector that detects the emission spectra from excited SERS probes. The device can further comprise at least one temperature control element integrated into the device or juxtaposed at a particular region of the device. In one aspect, the at least one temperature control element is distally located in the fluid flow channel. In another aspect, the at least one temperature control element comprises at least two temperature control elements. In yet a further aspect, the at least two temperature control elements are spaced apart, wherein a first element of the at least two temperature control elements is in juxtaposition with the free-surface interface region and the second element of the at least two temperature control elements is downstream of the first element in the fluid flow channel. In one aspect, the at least one free-surface interface region comprises dimensions such that a fluid in the at least one free-surface interface region is confined by surface tension. In a specific aspect, the at least one free-surface interface region comprises cross section dimensions from about 50 nm to about 1 mm. In yet another specific aspect, the at least one free-surface interface region comprises a length of about 1 μm to about 10 cm. In one aspect, the SERS probe comprises a nanoparticle, the nanoparticle may be a functionalized nanoparticle. The device may comprise a reservoir or multiple converging or diverging fluid flow channels for delivery, separation of different fluids or reagents. The fluid can be moved through the channel by for example, a pump such as a pressure driven, surface tension driven, thermal capillary-driven, or electrokinetically driven pump. In another aspect, the excitation region and detection region are optimized for SERS probe-analyte aggregation.

The disclosure also provides a method for analyte detection comprising: providing a flow of a fluid through a fluid channel in a fluidic device, the fluidic device comprising: a substrate; a fluid flow channel having a first end and a second end located in or on the substrate; at least one free-surface interface region located between the first end and the second end, wherein the free-surface interface region is open on at least one side to atmospheric air comprising an analyte; an excitation area, wherein electromagnetic energy excites a SERS probe in a fluid flowing in the fluid flow channel containing analytes; and a detection area, wherein an emitted spectra is detected by a detection device, wherein the free-surface interface region is in fluid communication with the excitation and detection areas and wherein analytes in the sample are absorbed into the fluid; an electromagnetic energy source that emits electromagnetic radiation at the excitation area; and a detector that detects the emission spectra from excited SERS probes, contacting the fluid with a SERS probe; and measuring emissions of SERS probes aggregated within the fluid with an analyte, wherein the emission spectra is indicative of the presence or type of analyte present in the sample. The device may further comprise an electromagnetic energy source that emits electromagnetic radiation at the excitation area. The device can further comprise a detector that detects the emission spectra from excited SERS probes. The device can further comprise at least one temperature control element integrated into the device or juxtaposed at a particular region of the device. In one aspect, the at least one temperature control element is distally located in the fluid flow channel. In another aspect, the at least one temperature control element comprises at least two temperature control elements. In yet a further aspect, the at least two temperature control elements are spaced apart, wherein a first element of the at least two temperature control elements is in juxtaposition with the free-surface interface region and the second element of the at least two temperature control elements is downstream of the first element in the fluid flow channel. In one aspect, the at least one free-surface interface region comprises dimensions such that a fluid in the at least one free-surface interface region is confined by surface tension. In a specific aspect, the at least one free-surface interface region comprises cross section dimensions from about 50 nm to about 1 mm. In yet another specific aspect, the at least one free-surface interface region comprises a length of about 1 μm to about 10 cm. In one aspect, the SERS probe comprises a nanoparticle, the nanoparticle may be a functionalized nanoparticle. The device may comprise a reservoir or multiple converging or diverging fluid flow channels for delivery, separation of different fluids or reagents. The fluid can be moved through the channel by for example, a pump such as a pressure driven, surface tension driven, thermal capillary-driven, or electrokinetically driven pump. In another aspect, the excitation region and detection region are optimized for SERS probe-analyte aggregation.

The disclosure also provides a method of discriminating a desired species in a sample, comprising: providing a flow medium comprising a SERS probe into a fluidic device comprising: a substrate; a fluid flow channel having a first end and a second end located in or on the substrate; at least one free-surface interface region located between the first end and the second end, wherein the free-surface interface region is open on at least one side to atmospheric air comprising a desired analyte species; an excitation area, wherein electromagnetic energy excites a SERS probe in a fluid flowing in the fluid flow channel containing analytes; and a detection area, wherein an emitted spectra is detected by a detection device, wherein the free-surface interface region is in fluid communication with the excitation and detection areas and wherein analytes in the sample are absorbed into the fluid; flowing the flow medium through a fluid flow channel of the fluidic device wherein analytes in a sample can be absorbed, adsorbed or bound in the flow medium at the free-surface interface region; applying an excitation electromagnetic radiation to the flow medium at or distal to the free-surface interface region; and detecting aggregation of the SERS probe with an analyte in the sample, wherein the emission spectra from the SERS probe is indicative of a species of analyte. The device may further comprise an electromagnetic energy source that emits electromagnetic radiation at the excitation area. The device can further comprise a detector that detects the emission spectra from excited SERS probes. The device can further comprise at least one temperature control element integrated into the device or juxtaposed at a particular region of the device. In one aspect, the at least one temperature control element is distally located in the fluid flow channel. In another aspect, the at least one temperature control element comprises at least two temperature control elements. In yet a further aspect, the at least two temperature control elements are spaced apart, wherein a first element of the at least two temperature control elements is in juxtaposition with the free-surface interface region and the second element of the at least two temperature control elements is downstream of the first element in the fluid flow channel. In one aspect, the at least one free-surface interface region comprises dimensions such that a fluid in the at least one free-surface interface region is confined by surface tension. In a specific aspect, the at least one free-surface interface region comprises cross section dimensions from about 50 nm to about 1 mm. In yet another specific aspect, the at least one free-surface interface region comprises a length of about 1 μm to about 10 cm. In one aspect, the SERS probe comprises a nanoparticle, the nanoparticle may be a functionalized nanoparticle. The device may comprise a reservoir or multiple converging or diverging fluid flow channels for delivery, separation of different fluids or reagents. The fluid can be moved through the channel by for example, a pump such as a pressure driven, surface tension driven, thermal capillary-driven, or electrokinetically driven pump. In another aspect, the excitation region and detection region are optimized for SERS probe-analyte aggregation.

The disclosure also provides a method for diagnosing a condition in a subject indicated by the presence of a species in a sample, comprising: introducing a flow medium comprising a SERS probe into a fluidic device comprising: a substrate; a fluid flow channel having a first end and a second end located in or on the substrate; at least one free-surface interface region located between the first end and the second end, wherein the free-surface interface region is open on at least one side to atmospheric air comprising an analyte; an excitation area, wherein electromagnetic energy excites a SERS probe in a fluid flowing in the fluid flow channel containing analytes; and a detection area, wherein an emitted spectra is detected by a detection device, wherein the free-surface interface region is in fluid communication with the excitation and detection areas and wherein analytes in the sample are absorbed into the fluid; flowing the flow medium through a fluid flow channel of the fluidic device wherein analytes in a sample can be absorbed, adsorbed or bound in the flow medium at the free-surface interface region; applying an excitation electromagnetic radiation to the flow medium at or distal to the free-surface interface region; and detecting aggregation of the SERS probe with an analyte in the sample, wherein the emission spectra from the SERS probe is indicative of a species of analyte.

The disclosure also provides a system comprising: a microfluidic device comprising: a substrate; a fluid flow channel having a first end and a second end located in or on the substrate; at least one free-surface interface region located between the first end and the second end, wherein the free-surface interface region is open on at least one side to atmospheric air comprising an analyte; an excitation area, wherein electromagnetic energy excites a probe in communication with a fluid flowing in the fluid flow channel containing analytes; and a detection area, wherein an emitted spectra is detected by a detection device, wherein the free-surface interface region is in fluid communication with the excitation and detection areas and wherein analytes in the sample are absorbed into the fluid; a detection device that detects the presence of analyte species by a method selected from the group consisting of Raman spectroscopy or SERS measurements on a substrate fixed to the microchannel walls or in the bulk liquid solution contained within the microchannel, electrochemical analysis techniques, fluorescent chemical marker techniques, fluorescence quenching, redox-labeled nucleic acid binding techniques including but not limited to the molecules DNA, RNA and PNA, X-Ray absorption techniques, IR, visible, UV, and other electromagnetic radiation absorption techniques, mass spectroscopy techniques, liquid chromatography techniques, flame ionization analysis techniques, DNA melting point techniques, or titration analysis techniques.

A system comprising: a microfluidic device comprising: a substrate; a fluid channel located in or on the substrate; at least one free-surface interface region, wherein the free-surface interface region is open on at least one side to atmospheric air comprising an analyte; a detection area, wherein the analyte can be detected by a detection device, wherein the free-surface interface region is in fluid communication with the detection areas and wherein analytes in the sample are absorbed into the fluid.

The details of one or more embodiments are set forth in the accompanying drawings and the description below. Other features, objects, and advantages will be apparent from the description and drawings, and from the claims.

Figure 1A:
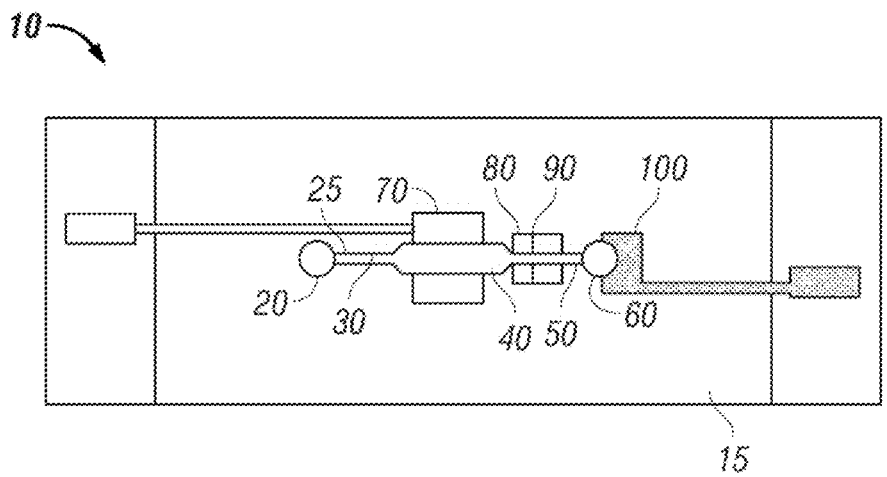
FIG. 1A-D depicts an embodiment of the disclosure showing a free-surface microfluidic platform. Surface tension is a dominant force at the micron length scales. The surface tension force can create significant pressure gradients that drive the flow and maintain stability of the free surface. The free-surface allows for direct absorption of airborne chemical agents directly into the aqueous working fluid. In an aspect, depicted in (C-D) absorbed molecules aggregate with colloidal particles to create a SERS effect. As the particles advect downstream, colloidal aggregation increases. An increase in SERS signal is obtained from nanoparticle aggregates.

FIG. 2A-C are schematics of a free-surface microfluidic device of the disclosure comprising systems to promote fluid flow by evaporative capacity. (A) and (B) are depictions of a device of the disclosure comprising temperature control elements. (C) shows a micrograph of a device comprising a dimension change to increase evaporation by splitting the stream.

FIG. 3A-B show a device of the disclosure. A) is a confocal microscope image of a free-surface fluidic channel. The channel is etched in silicon and is 15 μm wide and 1.4 μm deep. Similar channels can operate at ~100 nm depth. B) is a schematic of microfluidic sensor for analysis of gas-phase species. The free-surface liquid/atmosphere interface allows analyte absorption and subsequent optical stimulation with a $\lambda=514.5$ nm laser for SERS detection.

FIG. 4 is a cross sectional profile of the free-surface fluidic channel measured using confocal microscopy. The resolution in the vertical direction is ~10 nm. The radius of curvature of the free surface is estimated to be about 500 μm. The free surface is confined by surface tension, and can provide a means for absorbing airborne agents into the fluid flow channel flow.

FIG. 5 shows micro-PIV measurements of pressure-driven flow in a free-surface microfluidic channel. The velocity profile is peaked in part because of the variation in free-surface elevation. In this case, the maximum velocity is 100 um/s.

FIG. 6A-C shows schematics of an embodiment of the Free Surface microFluidic (FSF) channels. The fluid is confined by surface tension and the hydrophobic surface on the outside of the channel: (a) shows a rectangular fluid flow channel with straight side walls, (b) shows an undercut fluid flow channel. This creates a sharp corner which causes the contact line to be more stable and provides improved stability of the free surface flow, (c) shows a channel comprising two walls wherein a fluid between the two walls is held by surface tension.

FIG. 7 shows characteristic 4-ABT spectrum obtained by SERS in the open channel microflow (light gray/red line). Background SERS spectrum of the bare channel with no Ag-colloid or 4-ABT present (black line). SERS measurements were collected over a 1 second integration period with ~50 mW of laser power.

FIG. 8 shows the measured SERS intensity above a diagrammatic side view of the fluid flow channel (triangles, inverted triangles, circles). The aggregation simulation (solid line) assumes SERS intensity is due exclusively to nanoparticle dimers.

FIG. 9 shows the schematics of a Membrane Confined Fluidics (MCF). The fluid is confined by a semi-permeable membrane. The membrane allows airborne analyte to diffuse through to the microfluidic channel, where it is analyzed using SERS.

FIG. 10 shows a schematic of an Enclosed Fluid flow channel Fluidic (EMF) embodiment. Here the sample is introduced to the nanoparticle solution inside an enclosed microfluidic channel. This can occur (but not limited to) using a T-junction. SERS hot-spot formation occurs as the sample molecules interact with the nano-particle solution.

FIG. 11 shows an example of a suspended soap film. The soap film can contain SERS nanoparticles. When the nanoparticles are exposed to airborne molecules, they aggregate and form a SERS 'hot spot'.

FIG. 12 shows a graph indicating detection of RDX, Picric Acid, DNT, and 4-ABT vapor by a free-surface microfluidic device of the disclosure using Ag-colloid SERS at room temperature.

FIG. 13 shows detection of cocaine vapor by a free-surface microfluidic channel using Ag-colloid SERS at room temperature. Cocaine SERS spectrum obtained from a 1 mM solution of cocaine in water (middle line). Cocaine vapor SERS spectrum obtained by placing a small (<0.1 g) cocaine at several centimeters from the free-surface microfluidic SERS detection system (top line). All measurements were performed at room temperature.

FIG. 14 shows a graph of velocity vs. heater block input (Watts) for a 15 micron wide, 2 micron deep silicon open microchannel. In this case, the fluid is a silver nanoparticle suspension. The measured velocities were determined by micro-PIV.

FIG. 15 shows the detection of 2,4-DNT vapor is unaffected by a saturated gasoline environment above the open channel microfluidic SERS detection system. 2,4-DNT vapor was detected at room temperature with Ag nanoparticle SERS in a typical atmospheric environment (top line). 2,4-DNT vapor was detected at room temperature with Ag nanoparticle SERS while the local atmospheric environment above the detector was saturated with gasoline vapor (middle line).

FIG. 16 shows a typical series of SERS spectra, obtained by the stepwise measurement of Raman scattering along the microchannel in 10 μm increments, is shown as a function of position down the streamwise direction of the microchannel. The SERS interrogation path down the central region of the microchannel is shown (straight green line).

FIG. 17A-D shows a schematic formation of nanoparticle aggregates by the stepwise addition of adsorbate molecules (red spheres). A) Initial unbound state of the nanoparticles. B) A single nanoparticle is bound to an adsorbate molecule, forming a monomer. C) Two nanoparticles are bound to a single adsorbate molecule, forming a dimer. D) Three nanoparticles are bound to two adsorbate molecules, forming a trimer.

DETAILED DESCRIPTION

As used herein and in the appended claims, the singular forms "a," "and," and "the" include plural referents unless the context clearly dictates otherwise. Thus, for example, reference to "an analyte" includes a plurality of such analytes and reference to "the particle" includes reference to one or more particles (e.g., nanoparticles) known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications described herein are provided solely for their disclosure prior to the filing date of the present application. Nothing herein is to be construed as an admission that the inventors are not entitled to antedate such disclosure.

Stimulated neutron analysis systems and electron capture devices exist to identify explosives, but are limited to detection of large samples; the size and cost of these systems has limited their application in most settings.

Other currently available detection devices rely on mass spectrometry or ion mobility spectrometry to identify agents. This technique relies on identification of species by mass/charge ratios which do not provide molecular specificity. The current sensitivity of these devices is in the nanogram to pictogram range. Efforts to improve the signal-to-noise ratio in mass spectrometry or ion mobility spectrometry devices have recently improved the sensitivity of these devices but the fundamental limitations of false positive identification and large necessary target mass remain.

Techniques for label-free single molecule level detection and recognition of specific molecules or biomolecules are important in defense, medical, and environmental sensing applications. In this field, optical methods based on spectroscopy have been predominant owing to their non-destructive nature. Especially promising methods are label-free schemes such as Raman or extinction spectroscopy. Recently these spectroscopic techniques gain reinforced interests due to technical advances in metallic nanostructures. Under optical excitations of proper frequency, a metallic nanostructure sustains a plasmon resonance that results in highly enhanced local electromagnetic fields and distinct spectral extinction characteristics. For sensing applications, the field enhancement is utilized for surface-enhanced Raman spectroscopy (SERS) and the spectral extinction characteristics are used to detect the changes in local refractive index. The plasmon resonance characteristic depends on the topology of each nanostructure.

Normal Raman scattering is a scattering process in which photons incident on a sample transfer energy to or from the sample's vibrational or rotational modes. Individual bands in a Raman spectrum are characteristic of specific molecular motions. As a result, each of a plurality of analytes has its own unique Raman signature. When a Raman-active molecule is positioned within an electromagnetic field generated upon excitation of the localized surface-plasmon resonance of a nanostructure, the Raman signal increases by multiple folds of magnitude.

Raman imaging of living cells can nondestructively probe the intracellular biochemical dynamics without prior fluorescent or radioactive labeling, but the formidably low efficiency of Raman scattering hinders its applications in the detection of molecules at micromolar or lower concentrations. However, SERS by metallic nanostructures increases the original Raman scattering intensity many orders of magnitude, which makes the Raman detection of low concentration molecules practical.

SERS retains all of the advantages of normal Raman spectroscopy while achieving significantly stronger signal intensity. SERS is a process whereby the Raman scattering signal is increased when a Raman-active molecule is spatially confined within range of the electromagnetic fields generated upon excitation of the localized surface plasmon resonance of nanostructured metal surfaces. Both chemical and conformational information can be elucidated from SERS. Accordingly, SERS possesses many desirable characteristics as a tool for the chemical analysis of molecular species including high specificity, attomole to high zeptomole mass sensitivity, micromolar to picomolar concentration sensitivity, and interfacial generality.

The signature of a noble metal nanostructure is the localized surface plasmon resonance. This resonance occurs when the correct wavelength of electromagnetic energy (e.g., light) strikes a noble metal nanostructure causing the plasma of conduction electrons to oscillate collectively. The resonance oscillation is localized near the surface region of the nanostructure. Such resonance is advantageous in that the nanostructure is selectively excited at a particular photon absorption, which results in the generation of locally enhanced or amplified electromagnetic fields at the nanostructure surface. The resonance for noble metal nanostructures (e.g., in the 10-500 nm range, typically about 20-200 nm) occurs in the visible and IR regions of the spectrum and can be measured by UV-visible-IR extinction spectroscopy. The location of the resonance is related to the resulting SERS spectrum.

Colloidal Au or Ag nanoparticle clusters are commonly used as SERS substrates, and Raman enhancement factors as high as $10^{14}$ have been reported in single-molecular-level detections. Au and Ag nanoparticles are also utilized in Raman imaging to enhance signal intensity and increase image contrast. Strong Raman enhancement relies on distance-dependent electromagnetic field coupling between adjacent nanoparticles, so called "hot spots".

During the past fifteen years, there has been significant development in using micro/nanofluidic-based platforms for detection of chemical and biological agents. These platforms show high sensitivity, reduced sample size and reagent volume. In addition, microfluidic devices have the potential to be field-portable detection platforms. However, all the 'lab on a chip' platforms reported in the literature can process samples after the sample is injected into the fluid flow channel. No integrated device currently exists for capturing airborne agents directly into a fluid flow channel. This has limited the viability of 'lab on a chip' platforms for monitoring of airborne species.

It is difficult to deposit surface chemistry inside enclosed microchannels. It is difficult to introduce one chemical agent, and then introduce a second chemical agent, have them mix in a controlled fashion and then immobilize on a surface. In the case of large numbers of immuno-assays for array-type chips, the problem is further compounded by a large number of flow channels and large number of chemical species that must be introduced. This problem is solved using free-surface microchannels of the disclosure, which allows a variety of chemical deposition techniques to be incorporated to immobilize chemistry directly on the fluid flow channel surfaces.

In traditional microfluidics, the microchannels are enclosed on all sides of a fluid. The process of enclosing the fluid flow channel typically involves bonding a glass coverslip, glass wafer or plastic wafer to the existing part of the channel to seal the channel. The high temperatures required in the bonding process are often incompatible with the immobilized surface chemistry, rendering this approach unfeasible. Another advantage of Free-surface microchannels is that it can be used instead of the high temperature bonding processes that damage the chemistry.

Furthermore, the diameters of typically pipetted droplets are of order of millimeters. These volumes are at least an order of magnitude larger than what is commonly required for analysis. By providing multiple channel configurations in an embodiment of the detection system of the disclosure (e.g., arranging ~10 channels in a radial configuration), a droplet can be deposited onto a chip, and subsequently divided into 10 streams, each containing $\frac{1}{10}^{th}$ of the initial droplet. Fluid in the unused channels can be simply evaporated. Fluid in the remaining channels can then be transported in the chip for processing.

The SERS-based free-surface fluidics of the disclosure have the advantage of automatically collecting, and then detecting the analytes of interest, allowing facile quantification.

Free-surface fluidic (FSF) devices of the disclosure represent a new paradigm in microfluidic technology. The free-surface fluidic architecture uses surface tension to confine the fluid flow channel flow. The FSF architecture allows one or more surfaces of the microfluidic flow to be exposed to the atmosphere. Since the length scale is on the order of a few microns, a very large surface area is exposed to the atmosphere. This provides automatic injection of airborne molecules into the microfluidic channel. In addition, one advantage of the free-surface fluidic interface is the ability to filter interferent molecules, and the ability to concentrate airborne analyte molecules. Many interferent molecules may be hydrophobic, which can limit partitioning through the free surface and into the microchannel flow. Analyte molecules that are hydrophilic or at least partially hydrophilic will partition through the free surface and into the microchannel flow, according to Henry's law. As a result of partitioning into a condensed medium, such as water, trace concentrations of airborne analytes can partition with relatively high concentrations in a condensed medium. As a result, the free-surface fluidic architecture can effectively concentrate airborne molecules.

The microchannel flow has an advantage in that it can be used to control aggregation of (surface enhanced Raman spectrum) SERS-active probe particles in the flow. When analyte first interacts with a SERS-active probe particle, a monomer may be formed that provides surfaced-enhanced amplification of the signal. As the monomer advects downstream through the microchannel, the monomers aggregate into dimers that consists of two SERS-active particles sandwiching the analyte, which further increases the SERS amplification by several orders of magnitude. This gives rise to the so-called SERS 'hot spots'. As the particles advect further downstream through the microchannel, they aggregate into higher order clusters, such as trimers, etc., thereby decreasing the SERS amplification effect. Control of SERS-active particle aggregation allows for the maximum SERS amplification to be fully utilized, thereby enabling extremely high sensitivity detection of analyte.

Another advantage is that the microchannel flow enables continuous advection of SERS-active nanoparticles in the flow. This allows for new 'fresh' SERS-active probes to be continuously introduced to the analyte. As a result, the detector continually refreshes and can therefore operate in a sustained manner for relatively long periods of time.
Another advantage of conducting SERS-based interrogation of analyte in a condensed medium, such as water, is that it limits thermal derogation of analyte, which improves the quality, and signal to noise ratio, of the resulting Raman spectrum.

The resulting Raman or IR signal, can be recorded by suitable electro-magnetic detectors, and the spectra recorded by a variety of spectrometers. The resulting spectra can then be digitally analyzed using commercially-available or proprietary software to deduce the chemical composition of the analyte, based upon the emitted electromagnetic signal.

The control of SERS hot spot formation is one of the major challenges in SERS research and has limited its use as a commercial technique. The FSF architecture is ideal for tracking and deterministically controlling colloidal aggregation, allowing one to optimize and control SERS 'hot spot' formation, which leads to the controlled production of very large SERS intensity enhancement (e.g., up to 14 orders of magnitude increase in signal compared to normal Raman scattering).

The FSF architecture can act as a SERS-based gas sensor in which the evolution of hot particles is controlled by geometry and flow parameters. FSF architecture can be designed based upon aggregation modeling. For example, one can model and quantify the dynamics of aggregation and resulting Raman signal intensity in the design of microfluidic dimensions and excitation and sensing areas in a fluid flow. The concentration of gas-phase molecules absorbed into the nanoparticle flow is related to the partial pressure of the gas-phase species above the free liquid surface by Henry's law. Once absorbed, the molecules drive nanoparticle aggregation kinetics according to the rate equation $$k=k_o e^{-V_o/(K_b T(1+\beta m)^{12/5})} \quad [1]$$

where $k_o$ and $V_o$ are constants, m is the concentration of analyte in solution, and β is a temperature-dependent constant. At constant temperature, the gas-phase partial pressure of the target molecules affects the rate of formation of SERS-active nanoparticle aggregates through its effect on m in Eq. 1. When the concentration of the dissolved analyte is high, the nanoparticle aggregation rate approaches $k_o$ independent of analyte concentration. Consequently beyond a certain analyte concentration and its corresponding gas-phase partial pressure the observed maximum SERS intensity becomes more or less independent of the exposure time of the colloid to the analyte. At low values of m, however, the position of the SERS maximum in the microchannel will depend on m.

As shown in FIG. 8, SERS intensity versus flow-time curve can be developed and readily explained in terms of nanoparticle aggregation kinetics. The nanoparticle aggregation process is shown schematically in FIG. 17. The nanoparticles are originally in free suspension (FIG. 17A). The molecule 4-ABT is used merely to illustrate the working concept of this embodiment, however many other molecules or chemical compositions can be used, such as but not limited to, narcotics, explosives, etc. When 4-ABT is introduced into the flowing solution through the free-surface interface, 4-ABT binds to the nanoparticles, initiating the aggregation process. Monomers (FIG. 17B) form dimers (FIG. 17C), which, in turn, form trimers (FIG. 17D), and so on. Ag particle-adsorbate dimers (FIG. 17C) are ~3-4 orders of magnitude more SERS active than monomers (FIG. 17B). Likewise, the SERS responses of aggregate assemblies of more than two nanoparticles (e.g. trimers, FIG. 17D) normally have SERS cross-sections that are somewhat smaller (on a per adsorbed molecule basis) than that of the dimers.

The free-surface colloid aggregation process can be simulated, for example, using Comsol Multiphysics V 3.3 (*COMSOL, Inc. Stockholm, Se*). Diffusion constants for one- to four-nanoparticle aggregates were calculated from the Stokes-Einstein equation by using the geometric mean aggregate diameter. Since the diffusivity decreases for increasing aggregate size, the nanoparticle aggregation kinetics decrease with increased aggregate size.

The convection and diffusion equation for nanoparticle aggregate concentration $$\frac{\partial C_i}{\partial t} + (u \cdot \nabla)C_i = \nabla \cdot (D_i \nabla C_i) + R_i \quad (2)$$

was solved in two-dimensional space according to the reaction equations $$R_1=-2k(C_1C_1)-k(C_2C_1)-k(C_3C_1$$

$$R_2=k(C_1C_1)-k(C_2C_1)-2k(C_2C_2)$$

$$R_3=k(C_2C_1)-k(C_3C_1)$$

$$R_4=k(C_3C_1)+k(C_2C_2) \quad (3)$$

where $C_1$ is the concentration of unbound nanoparticles (FIG. 17A), $C_2$ is the concentration of nanoparticle dimers (FIG. 17C), $C_3$ is the concentration of nanoparticle trimers (FIG. 17D), $C_4$ is the concentration of nanoparticle tetramers, and $D_i$ is the respective nanoparticle-aggregate diffusivity. The Navier-Stokes and conservation of mass equations were used to find the flow velocity u, and k is the nanoparticle aggregation rate constant of Eq. 1. Using such calculations, a rate of analyte adsorption to a nanoparticle can be calculated. For example, the adsorption rate of 4-ABT adsorption to the Ag nanoparticles was assumed to dominate the analyte-particle desorption coefficient. For 4ABT, the value $k=10^6$ $m^3$/mol-s was chosen, as it compares well with the experimental SERS intensity data shown in FIG. 8.

As shown in FIG. 8, experimental data as well as simulation results demonstrate the advantage of using the free-surface microfluidic system to conform the otherwise stochastic process of aggregation kinetics into a spatially-deterministic process, where the greatest 'hot spot' concentration within the microchannel occurs at a controlled streamwise position. In FIG. 8, this position of greatest 'hot spot' concentration occurs at $x_e$=50 um, indicating this position in the flow will produce the greatest SERS enhancement of molecules detected in the stream. By this process, the present system for the first time allows for the maximization of detector sensitivity of a nanoparticle-activated SERS-based detector.

The free-surface fluidic architecture is combined with SERS for direct molecular-specific detection of airborne agents, such as explosives (e.g., 4-ABT (a molecule similar in structure to TNT)) with minimal user interaction. Another advantage of controlling nanoparticle aggregation, by using a flowing stream of colloidal particles in the microfluidic system disclosed here, allows the optimized molecular specific detection of gas-phase or airborne molecules.

The disclosure provides a system comprising: a microfluidic device having at least one open channel where at least one surface of a fluid is exposed to the surrounding atmosphere. The channel can contain a flowing or non-flowing liquid. The surface tension between the fluid and surrounding atmosphere is used to confine the flow. The free-surface can allow airborne agents to absorb into the fluid, where they can be detected.

The disclosure provides a system comprising a microfluidic device having a free-surface interface region, wherein a fluid interacts with analytes in a sample that comes into contact with the fluid and analytes in the sample are absorbed into the fluid; an excitation region, wherein a electromagnetic energy excites a SERS probe in the fluid containing analytes; and a detection region, wherein an emitted spectra is detected by a detection device, wherein the free-surface interface region in fluid communication with the excitation and detection areas; an electromagnetic energy source that emits electromagnetic radiation at the excitation area; and a detector that detects the emission spectra from excited SERS probes.

The disclosure also provides a method for analyte detection comprising maintaining a flow of a fluid through a micro- or nano-channel in a fluidic device, the fluidic device comprising a free-surface interface region, wherein a fluid interacts with analytes in a sample that comes into contact with the fluid and analytes in the sample are absorbed into the fluid. The free-surface interface region comprises a free surface of a fluid that is confined by surface tension.

The disclosure also provides a method for analyte detection comprising maintaining a flow of a fluid through a micro- or nano-channel in a fluidic device, the fluidic device comprising a free-surface interface region, wherein a fluid interacts with analytes in a sample that comes into contact with the fluid and analytes in the sample are absorbed into the fluid; a excitation region, wherein a electromagnetic energy excites a SERS probe in the fluid containing analytes; and a detection region, wherein an emitted spectra is detected by a detection device, wherein the free-surface interface region in fluid communication with the excitation and detection regions; an electromagnetic energy source that emits electromagnetic radiation at the excitation area; and a detector that detects the emission spectra from excited SERS probes, contacting the fluid with a SERS probe; and measuring emissions of SERS probes aggregated within the fluid with an analyte, wherein the emission spectra is indicative of the presence or type of analyte present in the sample.

The disclosure further provides a method of discriminating a desired species in a sample, comprising introducing a flow medium comprising a SERS probe into a fluidic device comprising at least one inlet and at least one outlet; flowing the flow medium through a region of the fluidic device wherein analytes in a sample can be absorbed, adsorbed or bound in the flow medium; applying an excitation electromagnetic radiation to the flow medium; and detecting aggregation of the SERS probe with an analyte in the sample, wherein the emission spectra from the SERS probe is indicative of a species of analyte.

The disclosure provides a method for diagnosing a condition in a subject indicated by the presence of a species in a sample, comprising introducing a flow medium comprising a SERS probe into a fluidic device comprising at least one inlet and at least one outlet; flowing the flow medium through a region of the fluidic device wherein analytes in a sample can be absorbed, adsorbed or bound in the flow medium; applying an excitation electromagnetic radiation to the flow medium; and detecting aggregation of the SERS probe with an analyte in the sample, wherein the emission spectra from the SERS probe is indicative of a species of analyte, the species of analyte being associated with a disease or disorder.

In one aspect, the disclosure provides an integrated micro/nanofluidic platform that can monitor airborne molecules in real time. Free-surface fluidics allows airborne molecules, such as those of common explosives, biowarfare agents, contaminants, molecules from the breath, etc., to be captured at the fluid interface. Once absorbed into a fluid flowing in a fluid channel (e.g., a fluid flow channel or nanochannel), the analytes can be detected by a variety of techniques, one of which is Surface Enhanced Raman Spectroscopy (SERS).

FIG. 1A depicts a free-surface detection device of the disclosure. A free-surface detection device 10 comprises a substrate 15 upon which or within which a reservoir or inlet 20 is fluidly connected to an outlet 60 by a fluid channel 25. In one embodiment, the reservoir or inlet 20 is about 40 $\mu$m deep (e.g., 1-100 $\mu$m). Fluid channel 25 comprises contiguous different regions having a proximal fluid flow region 30, free-surface interface region 40 and distal fluid flow region 50. Also depicted in FIG. 1A are optional temperature control elements 70 and 100. FIG. 1A also identifies excitation region 80 and detection region 90, which, when present, are approximate locations in the distal fluid flow region 50, or in the free-surface interface region 40. Typically, regions 80 and 90 coincide. For example, when using Raman, fluorescent or IR spectroscopy, regions 80 and 90 coincide based upon excitation and emission timing.

Figure 3A:
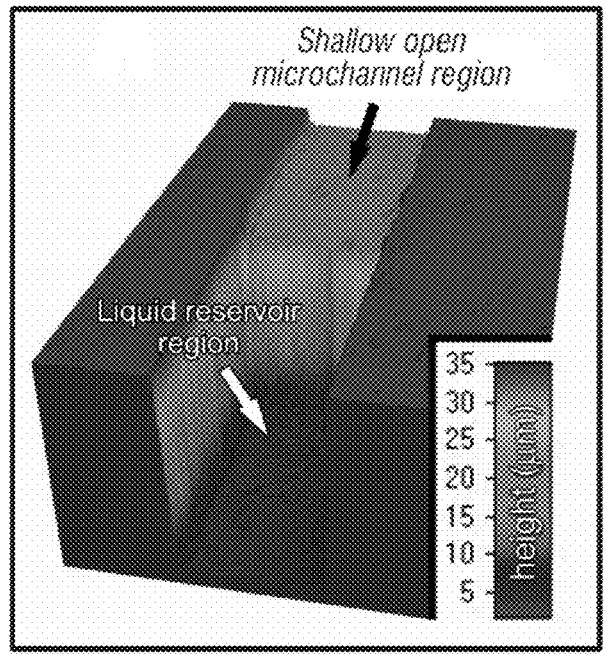
Figure 3B:
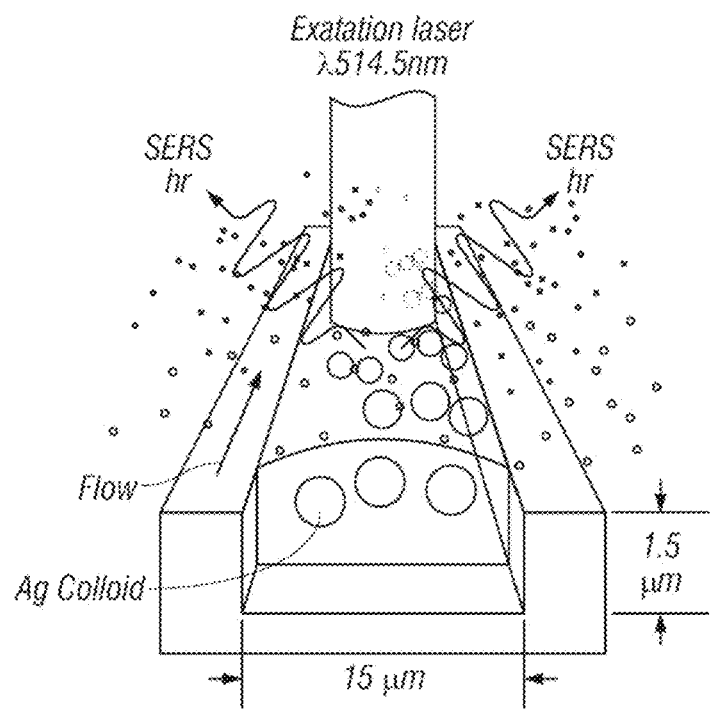

The fluid channel 25 cross section can take any number of geometries (e.g., rectangular, circular, oval, triangular and the like). Typically, a fluid flow channel is about 0.2 $\mu$m to 5 $\mu$m in depth (e.g., 0.3 $\mu$m, 0.4 $\mu$m, 0.5 $\mu$m, 0.6 $\mu$m, 0.7 $\mu$m, 0.8 $\mu$m, 0.9 $\mu$m, 1 $\mu$m, 1.1 $\mu$m, 1.2 $\mu$m, 1.3 $\mu$m, 1.4 $\mu$m, 1.6 $\mu$m, 1.8 $\mu$m, 2 $\mu$m, 3 $\mu$m, 4 $\mu$m, 5 $\mu$m, or greater in depth), with surface tension forces at the meniscus formed by the free surface being sufficient to confine the liquid in the channel, even when the fluid is pumped through the free-surface interface region 40 by an axial pressure gradient. Fluid with in the fluid flow channel 25 can be pumped via electrokinetic processes such as electroosmosis by an applied electric field, or by other means. FIG. 3 shows the dimensions of a free-surface detection device fluid flow channel, measured using confocal microscopy.

Figure 6A:
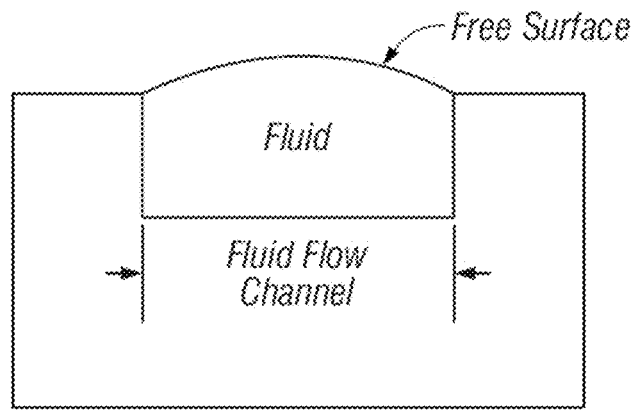
Figure 6B:
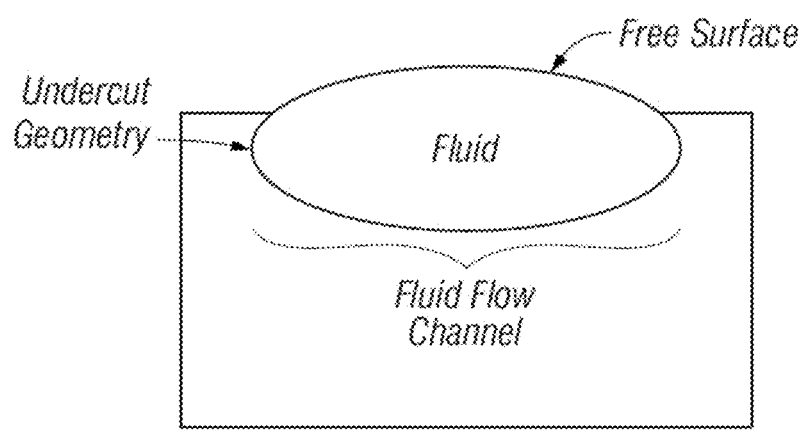
Figure 6C:
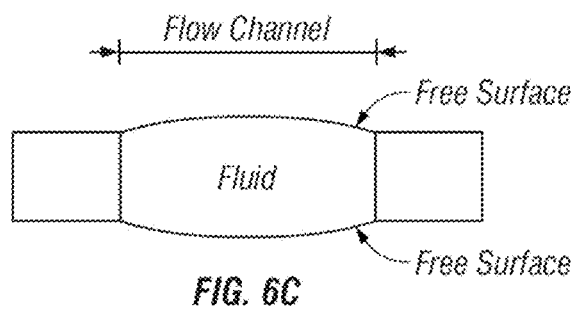

The fluid flow channel geometry and surface chemistry is optimized to obtain a desired sensor operating characteristics. For example, a deeper fluid flow channel will decrease the precision required for evaporation/condensation control, and increase flow rate; however, more shallow microchannels increase the effective sensitivity of SERS detection, increase the surface/volume ratio, and are more sensitive to surface tension effects. FIG. 6 depicts free surface fluid flow channel geometries. In FIG. 6a, the fluid flow channel is rectangular in shape (although other shapes/geometries can be used). The free surface is confined by surface tension and the hydrophobic surface outside the channel. In FIG. 6b, the fluid flow channel is undercut during the etching process. This creates a sharp corner which causes the contact line to be more stable and provide improved stability of the free surface flow. In FIG. 6c there is depicted a fluid channel comprising two walls such that the dimensions result in a liquid being held in the channel by surface tension. It will also be recognized that a fluid channel may be a single planar surface with a hydrophilic or hydrophobic (depending upon the fluid) region holding the fluid in place on the surface of the substrate. In another aspect, varying the width of the flow channel (e.g., increasing width in the fluid flow direction) causes a pressure gradient, causing liquid to flow towards the wider region. The width dimension of the fluid flow channel can be designed such that change in dimension between a narrower region that produces a higher Laplace pressure produces a liquid flow towards a wider region that produces a lower Laplace pressure. The dimensions of the free-surface channels can be used to stabilize the flow and optimize the detector performance. For example, shallow flow regions have the advantage of increasing analyte molecule concentration.

Electrowetting or other electro-potential methods can be used to control the wetting properties between the liquid and the solid substrate, thereby controlling the meniscus shape. This in turn can be used to control the local pressure distribution in the fluid, which can be used to control fluid motion.

Electrokinetic techniques are well known for pumping fluids, concentrate and separate molecules. For example, electroosmosis can be used to pump fluids in both free-surface and enclosed microchannels.

Standard electrophoretic separation and concentration techniques require DC Faraday currents. As a result, electrolysis produces hydrogen and oxygen gas at the electrode surfaces. At low current, this gas can be absorbed into the fluid. However, at higher currents, gas bubbles can form near the electrodes, thereby degrading system performance. In an open micro/nanofluidic channel, this gas can escape through the free-surface interface. Therefore, the electrodes can be placed at short separation distances in the channel, and operate with much lower voltages than the ~1 kV levels that are typically used to date.

The free-surface fluidics architecture allows for both the direct injection and the recovery of samples to/from mid-channel sections. Such injection and recovery can be performed immediately prior to and immediately after chemical separation and/or detection.

Free-surface regions in fluid flow channels allow direct electrochemical probing of the liquid in the channel with both DC and AC-coupled electrodes. The tips of these electrodes can be bare pure platinum wire (10 um diameter), while the rest of the tip can be coated with a hydrophobic dielectric layer to prevent water in the channel from wicking up into the probe. Such probes can be fabricated by thermally stripping dielectric layers from commercially available silica capillaries, custom coated with Teflon. To position and control such probes, one can leverage the already mature technology of probe stations for integrated circuits (with minor modifications such as incorporating these new electrodes). Multiple, reconfigurable probes can be inserted midstream into fluidic channels. This allows application of local fields for a variety of functions that can then be achieved by fully reconfigurable and movable mid-channel electrodes; including electrochemical detection, dielectrophoretic sample separation and control, electrokinetic instability-based rapid mixing, and local heating.

Two or more probes can be used to achieve dielectrophoretic concentration (via kHz to MHz fields to avoid electrolysis bubbles) and separation of particle analytes in mid-channel chambers and mid-channel sections. For example, under suppressed EOF conditions midchannel dielectrophoresis probes can be used to concentrate analytes that undergo positive dielectrophoresis as pressure driven flow drives the analyte stream. A high field current can be used to locally vaporize liquid in channels to momentarily affect a "fluidic interrupt" at any user specified location along the channel (midstream), and with negligible disturbance of the rest of the channel. Under active or suppressed EOF conditions, one can use small-gap, high field AC electric fields to affect localized, rapid micromixing by inducing electrokinetic flow instabilities.

It is desirable in micro/nanofluidics to implement fluidic valves that are reliable, robust, operate with low voltage, and have no moving parts. Currently, valves in micro/nanofluidics are often fabricated from one or more layers of PDMS. These valves can be difficult to fabricate, and require pneumatic actuation, which is typically not desirable for field-portable systems. The free-surface architecture allows for a new type of valve. An electrode can be used to locally heat the channel, thereby locally evaporating the fluid and dividing the channel into two or more segments of fluid—thereby creating a virtual valve. When the voltage across the electrode is reduced, the local region quickly cools allowing vapor to condense, reconnecting the fluid streams—thereby removing the virtual valve. In addition, local evaporation can also be used for controlled pumping of fluid, and concentrating molecular species.

Referring to FIGS. 1A-D, the fluid channel 25 comprises various regions comprising a proximal fluid flow region 30 and free-surface interface region 40 and a distal fluid flow region 50 that are in fluid communication with one another. Proximal fluid flow region 30 is downstream of inlet 20 and upstream of free-surface interface region 40. A proximal fluid flow region 30 comprises at least one wall defining an enclosed space in which a fluid can flow. In another aspect, the proximal and distal fluid flow regions (30 and 50, respectively) comprise at least one wall defining an enclosed space. The free-surface interface region 40 comprises at least one wall defining a fluid flow space that is not a fully enclosed space (e.g., is at least partially open to contact with a different fluid environment, such as atmospheric air). Although FIG. 1A depicts free-surface interface region 40 as having a different width, such a depiction is for ease of setting forth the various regions, the width of the free-surface interface region can be identical, substantially identical, larger or smaller than the width of the proximal and/or distal fluid flow regions 30 and 50, respectively. In one aspect, the distal fluid flow region 50, comprising the detection region in some embodiments, is about 15 μm wide and about 1.4 μm deep.

Temperature control element 70 is optionally present to control evaporation or condensation of fluid flowing through the fluid flow channel 25. In one aspect, temperature control element 70 comprises a cooling element that reduces the evaporative capacity of a fluid flowing through the system upstream of the free-surface interface region 40.

Temperature control element 100 is optionally present to control evaporation or condensation of fluid flowing through the fluid flow channel 25. In one aspect, temperature control element 100 comprises a heating element that increases the evaporative capacity of a fluid flowing through the system downstream of the free-surface interface region 40. In this manner, fluid can be pumped through the fluid flow channel 25 using evaporative/thermal capillary action.

Figure 2A:
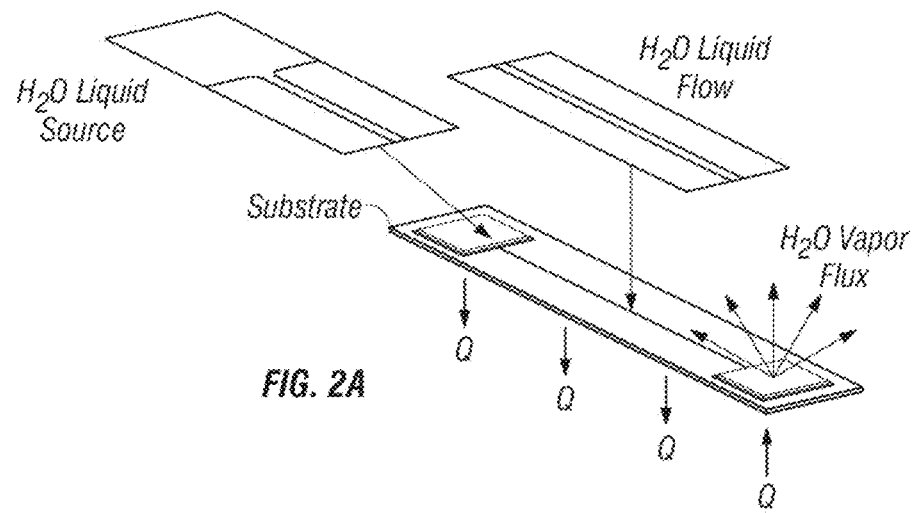
Figure 2B:
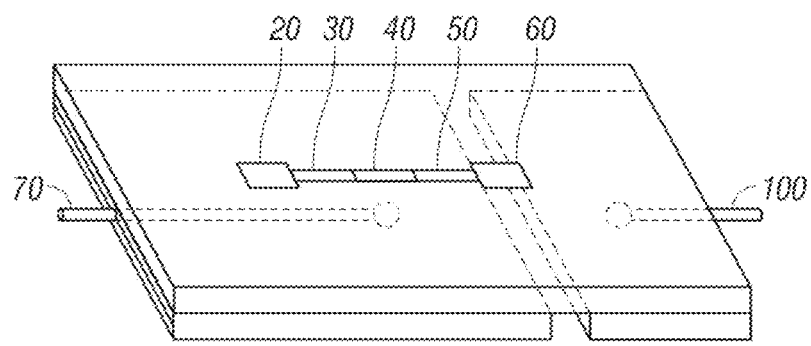
Figure 2C:
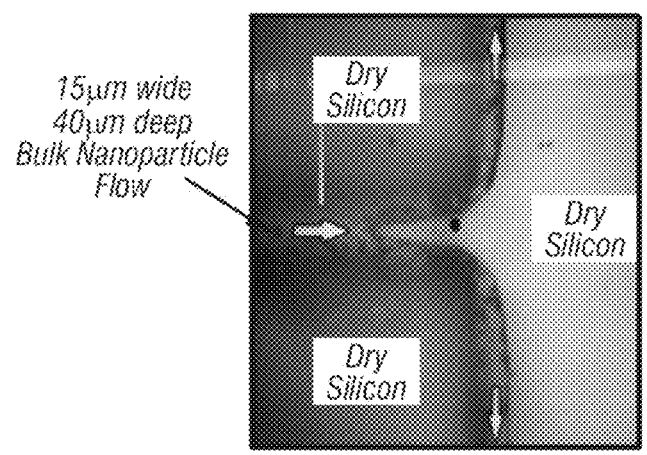

In some aspects, both temperature control elements 70 and 100 are present, wherein an upstream element 70 is a cooling element and the downstream element 100 is a heating element. The temperature profile between the liquid reservoir and the liquid evaporator region can be controlled to thereby control the vapor flux along the fluid flow channel and in the reservoir and evaporator. By maintaining the temperature near the dew point over the liquid reservoir and the open fluid flow channel, the flow is preserved in this region. By maintaining a temperature higher than the dew point in the evaporator, the vapor flux in this region causes liquid loss that then drives the fluid flow in the flow channel to flow by surface tension effects or thermal capillary action. By this means, a robust and controllable microsystem is possible to produce reproducible open fluid flow channel flow (see, e.g., FIGS. 2A-B).

The use of heat to control vapor flux is also useful to concentrate analyte species. For instance, an open fluid flow channel flow can be established at a temperature near the dew point in order to collect vapors from the surrounding environment, then the temperature of the silicon substrate can be raised. The raised temperature will thus increase the liquid vapor flux in this region, effectively concentrating the analyte species which are contained in the fluid flowing in the fluid flow channel. By this means, the open channel system is capable of concentrating the ambient chemical species within the fluid flow channel flow.

In yet a further aspect, the temperature control elements can be used to form evaporative sections or regions for SERS probing. Nanostructured templates can be added to the bottom of the free-surface interface region 40 of flow channel 25. The nanostructured templates are used to amplify the Raman scattering effect by inducing SERS. Fluid is flowed through the fluid flow channel 25 to condense gas-phase species into the channel. The fluid is then allowed to evaporate or is otherwise removed, for instance by lowering the local pressure, thereby allowing the analyte to deposit within the dry fluid flow channel and adsorb onto the dry nanostructured templates within the fluid flow channel. The nanotemplates are then interrogated by SERS to detect/measure the concentration of analyte deposited on or near the templates.

A thermal gradient can also be created along the fluid flow direction of the free-surface interaction region 40 such that a cool fluid stream passes over a distance of, for example, 0.5 mm. The temperature of the fluid may be maintained near the ambient dew point temperature. Analyte is adsorbed into the fluid stream. The stream is then subjected to a thermal gradient such that the temperature of the liquid rises as the liquid further down fluid flow path towards the distal region of the fluid flow channel. This causes the evaporation of liquid from the channel, thereby depositing the collected analyte molecules on the walls of the channel. Continuous deposition, and therefore an effect which concentrates the analyte molecules, thus occurs in the region of the channel where evaporation occurs. The channel surface may be coated with one or more nanostructured templates which amplify the Raman scattering strength of the deposited molecules. The temperature gradient can be caused by thermoelectric coolers/heaters, (e.g., Joule heating by passing an electrical current through a region of electrical resistance, or by Joule heating caused by the application of light such as from a laser). Further, the surface material can be colored to selectively warm particular regions when subjecting the surface to a light source. For instance, this effect can be caused by coloring some regions of the surface black and coloring other regions of the surface white.

Compartments or channel(s) in the free-fluid detection device of the disclosure can be actively cooled in order to prevent liquid evaporation. The compartment(s) or channel(s) can be exposed to the atmosphere over time to collect airborne samples. The compartment(s) or channel(s) can then be covered again to produce a 'time history' of the gas-phase species collected. The time history can then be re-analyzed again later, or used as evidence that the compounds which had absorbed into the volume were indeed present. The fluid in the compartment(s) or channel(s) could be frozen, for instance by a Peltier cooler, to preserve the integrity of the absorbed compounds.

Local Temperature can be monitored by platinum (or other material) electrodes, functioning as thermistors (RTDs). RTDs are standard temperature measuring devices, and will be usable in the free-surface fluidic architecture. The temperature can be controlled by using a cooling source, such as a Peltier Junction. Evaporation in the free surface fluidic environment can be controlled by controlling the temperature of the free-surface fluidic channel, or by controlling the relative humidity in the surrounding atmosphere.

The fluid flowing in a flow channel can be frozen, for instance by lowering the operating temperature by activating a nearby Peltier cooler which may be in contact with the fluidic chip or substrate. In this manner, fluid in the compartment(s) or flow channel(s) of the device (a) hold analyte species in a constant position for long-term chemosensing, for instance by SERS; (b) prevent thermal analyte degradation, for instance by the local heating effects caused by a SERS illumination laser; and/or (c) allow later analysis for evidence of the existence of the compound at the time of sensing.

Furthermore, flash freezing of a flow channel's or fluid compartment's content can be used for the controlled extraction of compounds from the flow. For instance, isotachophoresis can be used to concentrate proteins by a factor of $1 \times 10^6$ into a sub-micron band. Once the concentration of protein occurs, it can be flash frozen for later analysis by extraction through the free surface.

The flow channel's or fluid compartment's contents can be frozen to allow molecules, particles, or other species to accumulate on a solid surface. The frozen fluid can then be melted to allow the analyte to diffuse into the surface. A fluid which features a high-temperature melting point can be used to collect material on the solid surface at room temperature. The liquid can then be heated to cause melting and the subsequent diffusion of analyte into the liquid bulk. The liquid could then be analyzed by SERS or re-frozen in order to capture the analyte species.

Referring, again, to FIGS. 1A-D, a free-surface detection device 10 can also comprises an excitation region 80. The excitation region 80 may be may be integral to the free-surface interface region 40 or may be integral to the distal fluid flow region 50. In some embodiment, the excitation region 80, the detection region 90 and the free-surface interface region 40 can coincide. Where the distal fluid flow region 50 comprises an enclosed fluid flow channel, the excitation region 80 is substantially transparent to light or other electromagnetic radiation. A detection region 90 is downstream of the free-surface interaction region 40 and comprises a region in which a detector can measure a detectable signal indicative of the presence of an absorbed species in the fluid flow. Detection region 90 can be present alone or immediately downstream of the excitation region 80. Typically regions 80 and 90 coincide, e.g., when using Raman, fluorescence and IR spectroscopy.

Excitation of the nanostructures of the disclosure is performed by contacting the nanostructure with appropriate electromagnetic radiation (e.g., an excitation wavelength). Wavelengths in the visible spectrum comprise light radiation that contains wavelengths from approximately 360 nm to approximately 800 nm. Ultraviolet radiation comprises wavelengths less than that of visible light, but greater than that of X-rays, and the term "infrared spectrum" refers to radiation with wavelengths of greater 800 nm. Typically, the desired wavelength can be provided through standard laser and electromagnetic radiation techniques. In another aspect, a diffraction-limited excitation laser beam useful in the disclosure has a diameter of less than 1 µm, which can be scanned along the surface of a fluid flow channel, providing information regarding the partitioning of the analyte from the atmosphere into the aqueous phase of the colloid. The laser may operate at visible wavelengths, such as 488 nm, 514 nm, 532 nm, 633 nm, 785 nm, or 1064 nm.

Figure 1B:
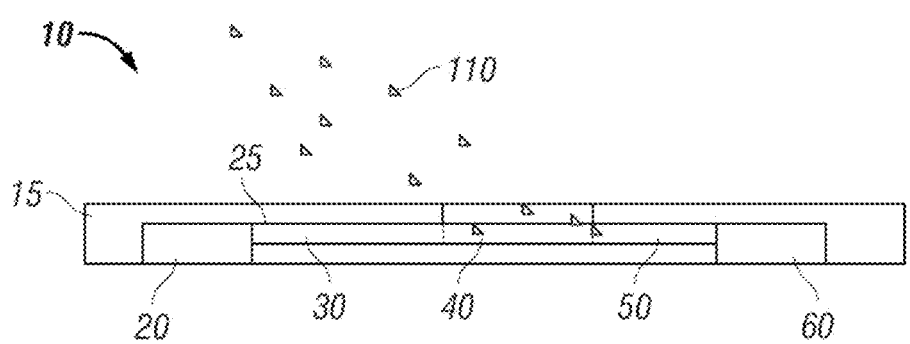
Figure 1C:
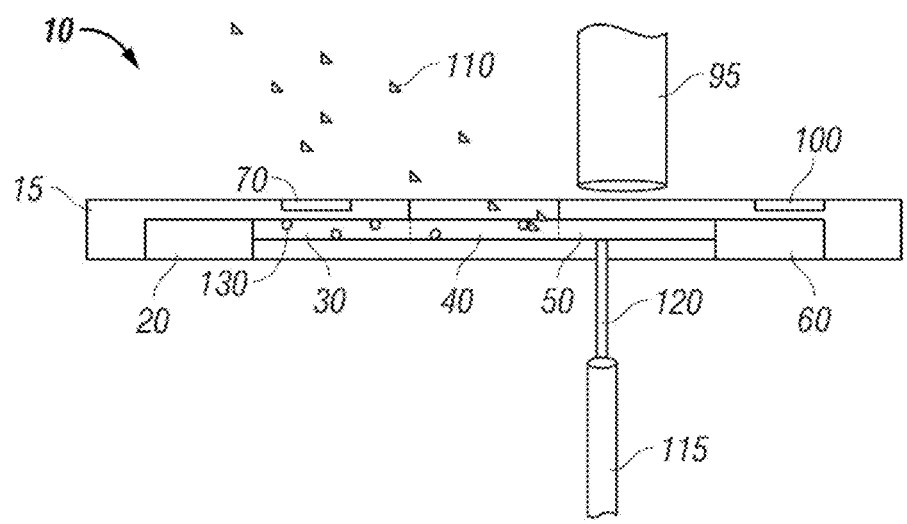

FIG. 1B-C show a side view depiction of a free-surface detection device 10. As described above, a substrate 15 comprises a reservoir or inlet 20 fluidly connected to an outlet 60 by a fluid channel 25. Fluid channel 25 comprises contiguous different regions having a proximal fluid flow region 30, free-surface interface region 40 and distal fluid flow region 50. Also depicted is analyte 110, which is capable of absorption into a fluid flowing through the fluid flow channel 25 at free-surface interaction region 40. A nanoparticle 130 is depicted in the fluid flow channel 25. The nanoparticle 130 is capable of interaction with analyte 110. Electromagnetic radiation 120 is generated by electromagnetic radiation generator 115 (e.g., a laser). A detector 95 is depicted adjacent to the electromagnetic radiation 120. Without loss of generality, the electromagnetic radiation 120 and detector 95 can also be placed adjacent to the free-surface interaction region 40 or adjacent to the distal region 50.

Figure 1D:
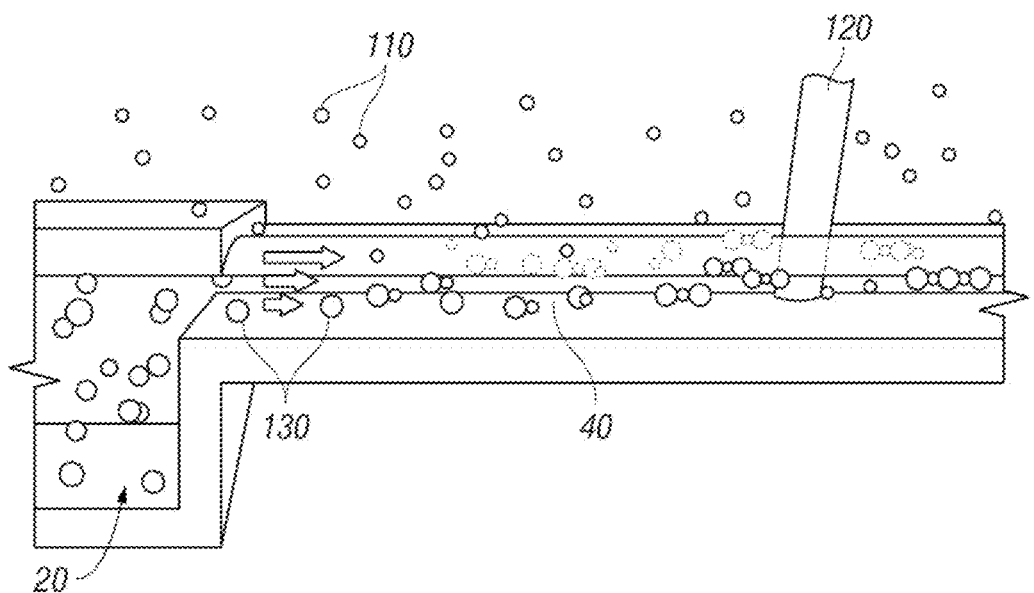

One embodiment of the disclosure is shown in FIG. 1D where the integrated free-surface microfluidic device 10 is combined with SERS for molecular-specific detection. The free-surface flow utilizes surface tension to create pressure-driven flow. Once absorbed through the surface at the free-surface interaction region 40, the analyte 110 (e.g., airborne molecules or particles) adsorb on a nanoparticle 130 (e.g., a silver nanoparticle). The nanoparticle-analyte complexes can undergo further aggregation that results in greatly-enhanced SERS effect (e.g., up to 14 orders of magnitude increase in signal over normal Raman scattering). As the nanoparticles 130 move downstream, colloidal particles continue to aggregate, where monomers form dimers, and dimers form trimers, and the like. One use of this disclosure is that the region of the greatest SERS intensity in a stream of flowing nanoparticles can be identified and therefore deliberately interrogated by SERS to provide optimized SERS sensitivity while performing SERS measurements.

Any device suitable for detection of a signal from the nanostructure of the disclosure. In some embodiments, the device includes delivery and collection optics, a laser source, a notch filter, and detector.

Infrared spectroscopy (IR) and surface-enhanced infrared spectroscopy (SEIRS) can be performed in free surface microfluidic channels. Much like the combination of SERS and free-surface microfluidic channels, IR and SEIRS can be used to detect exogenous agents which contact the free-surface flow. IR and SEIRS can also be used to detect exogenous agents which contact the nanostructured materials described in the disclosure. One benefit of using a free-surface flow for detection with IR and SEIRS is that an IR-transparent liquid can be used to transport agent for detection within an IR or SEIRS apparatus. Many common materials, such as amorphous glass ($SiO_2$) absorb in the infrared region, causing the loss of IR and SEIRS signals. In this case, the free-liquid surface allows the infrared-wavelength light to pass from the flowing liquid to the detector without unnecessary loss by absorption into a glass or similar channel boundary material. The free-liquid surface is also ideal for the absorption of analyte into the flowing stream. In this embodiment, the IR or SEIRS sensor device can be used for the real-time profiling of gas-phase or otherwise suspended compounds in the flowing liquid stream.

A variety of working fluids can be used in the sensor such as, but not limited to, water, silicon oil and glycerol. The fluid selected will be based on the partition coefficient of the analyte to be autoinjected (e.g., absorbed) into the fluid. In one embodiment, an aqueous solution is used. Low volatility liquids exhibit relatively low evaporation rates, and are therefore less sensitive to temperature fluctuations and are more stable for certain sensing applications.

The detection region is comprised of a portion of the fluid flow channel which is interrogated by an optical or other sensing system used for the detection of exogenous species by Raman, SERS, IR, or SEIRS spectroscopy. In one aspect, a mixing stream of a salt solution is used to promote SERS signaling. For example, in one aspect, one stream comprises a stable colloid solution, for instance comprised of silver nanoparticles, and the other stream comprises a salt solution. Since salt is useful in initiating aggregation of nanoparticles after mixing, the aggregation kinetics of these two streams evolves from a state of no aggregation to a state of aggregation which provides maximal SERS intensity. The feed ratio of the two streams can be controlled such that the sensor region features a nanoparticle stream which contains a fraction of salt ion that can be any value between 0% and a concentration high enough to quickly induce aggregation regardless of the presence of other aggregation-inducing species. With this arrangement, the salt concentration can be increased such that the salt induces aggregation and the formation of many crevices and adsorption sites for the SERS enhancement of exogenous species. Since the aggregation process is a function of time, and since time is evolved as the solution flows down the fluid flow path of the fluid flow channel, the evolution of the nanoparticle aggregate is resolved down the stream-wise direction of the fluid flow channel and the position of maximal SERS response can be identified by scanning with a SERS apparatus. By cycling the salt ratio while monitoring various fluid flow positions in the fluid flow channel, the SERS sensor can potentially detect local molecules regardless of their aggregation kinetics.

The combination of a flowing nanoparticle solution with a salt solution produces a stable source of clean colloid which flows into the detection region of the fluid flow channel. The salt induces nanoparticle aggregation regardless of the ability of the exogenous species to induce nanoparticle aggregation. This forms a SERS system based on colloid-formed hot spots which senses species that do not natively induce nanoparticle aggregation. The continuous supply of clean colloid into the system and the ability to fix the region of maximal hot spot activity via the interrogation by SERS of a fixed point in the fluid flow of the fluid flow channel allows the monitoring of exogenous agents over time while maintaining a fresh, uncontaminated, and controllable nanostructured substrate for SERS detection.

A gas flow can be used to cause fluid motion and changes in relative humidity above a surface wetted with a nanostructured colloid. This can cause the selective evaporation of colloid solvent, thereby causing the selective deposition of nanostructured materials suspended in the colloid for use with SERS. For instance, a nanomolar concentration colloid of 35 nm diameter silver particles can be applied to the surface of a silicon wafer, then a gas stream can be passed along the midstream of the wetted silicon surface. This causes the directed accumulation of silver particles in the two regions bisected by the gas flow. Further, the proper dimensioning of the regions can be controlled by designing a collection of gas streams to produce deterministically designed sizes by organizing a network of gas streams to cause the production of one or many micro-sized areas exhibiting SERS activity.

Once an open channel or free surface suspension of silver colloid is produced for use with SERS analysis, the passing of electrical current through the suspension by the application of two electrodes of dissimilar potential can be used to sense whether or not the surface is wetted and is ready for use. For instance, a feedback loop can be created such that a colloid solution is pumped into a microchannel for use with SERS analysis until the electric current which flow between two electrodes achieves a particular value. This application allows the real-time monitoring of the suitability of the wetted surface for SERS analysis by indicating the amount of colloid solution present at the surface or region. Accordingly, in one aspect the device can further comprise conductivity electrodes to measure the conductivity of a fluid comprising colloidal nanoparticles for use in SERS sensing. Typically, the electrodes will be disposed in the fluid flow channel and may be integrated into the at least one wall (on substantially opposite sides).

Not all airborne molecules impinging on the water/air interface cross the interface into the liquid phase. In fact, a great deal is known regarding the partitioning of molecules between a liquid and the atmosphere above it. This partitioning depends, in part, on the solubility of the molecule in the liquid and the propensity of the molecule to reside near the interface by virtue of its ability to reduce the interfacial free energy (Gibbs adsorption). These properties can be controlled, in part, by a judicious choice of liquid, which can be mixtures of water and other miscible liquids such as alcohols and ketones. This would sustain nanoparticles in stable colloidal solution while improving the degree to which the target analyte molecule dissolves in the liquid phase solution. For example, the selection of the flowing liquid medium can be made, for instance, based on polarity requirements to selectively absorb ambient chemical species into the flow. For instance, a hydrophilic medium such as water can be used within the channel for use in SERS measurements such that explosive molecules such as DNT will readily absorb into the flow for detection. However, non-polar molecules such as gasoline will not be absorbed into the flow, thereby minimizing contamination effects on the detector system. Subsequently, by using a free-surface channel, one can create analyte concentrations that are sufficiently large that makes SERS detection feasible, even at ppb levels.

Arrays and nanofluidic devices of SERS probes are also contemplated by the disclosure. The disclosure provides fluidic devices that can drive and guide liquid flow in microfluidic channels to transport biomolecules and living cells at controlled speeds and directions.

As polydimethylsiloxane (PDMS) microfluidic chips fabricated by soft lithography have been extensively used in chemical, biomolecular and cellular analysis, the disclosure demonstrates the optofluidic control of in PDMS microfluidic chips. Unlike the unconfined flow of a millimeter-scale liquid drop, the optically controlled fluidic flow in predefined microchannels is laminar and unidirectional. It shows a much higher flow speed as the vapor and droplets are bound within the channel and contribute to the liquid advance along the channel direction and the minimized vertical convection in microchannels favors the heat concentration at the liquid-air interface.

Microfluidic channels can be formed in any number of materials. Thus, the devices of the disclosure include at least one flow channel that allows the flow of sample to other channels, components or modules of the system. As will be appreciated by those in the art, the flow channels may be configured in a wide variety of ways, depending on the use of the channel. For example, a single flow channel starting at a sample inlet port may be separated into a variety of smaller channels, such that the original sample is divided into discrete subsamples for parallel processing or analysis. Alternatively, several flow channels from different modules, for example, the sample inlet port and a reagent storage module (e.g., a nanoparticle storage module) may feed together. As will be appreciated by those in the art, there are a large number of possible configurations; what is important is that the flow channels allow the movement of sample and reagents from one part of the device to another. For example, the path lengths of the flow channels may be altered as needed; for example, when mixing and timed reactions are required, longer flow channels can be used.

In one embodiment, the devices of the disclosure include at least one inlet port for the introduction of a sample to the device. This may be part of or separate from a sample introduction or a sample mixing chamber.

In another aspect of the disclosure, the devices of the disclosure may include a manipulation chamber that allows for the mixing of nanoparticle SERS probes and a fluid sample. Optionally, an aggregation stimulant (such as a salt) can be mixed in the manipulation chamber.

In addition to individual straight channels, a functional microfluidic circuit often consists of channel junctions. The positioning of liquid flow at channel junctions can include valve systems.

A fluid device of the disclosure comprises a substrate (which may be one or more substrates associated with one another to define fluid channels there between). The fluid device can comprises a sample inlet in fluid communication with sample fluid flow channel and buffer inlet in fluid communication with buffer fluid flow channel.

In one embodiment, substrate comprises an insulating (e.g. glass or polymer), or a semiconducting (e.g. silicon structures) in which various features (e.g., channels, chambers, valves and the like) are designed. Such features can be made by forming those features into a surface and/or a subsurface structure of substrate using microfabrication techniques known to those skilled in the art.

By extending the above channels and adding more sorting regions downstream, the disclosure provides sorting devices with multi-stage purification. In one aspect, the disclosure provides methods and systems that utilize massive parallelism and multistaging. This allows full utilization of the central benefits of microfabrication technology to achieve high throughput, purity and recovery simultaneously.

Microfabrication technologies provide the ability to implement multiple staging and massive parallelism on a single chip, thus allowing for the production of inexpensive, disposable, flexible, and portable devices.

A fluid flow channel comprising a nanostructured template can be formed using techniques known in the art. For example, the channel can be filled with a masking material such as photoresist. The surface of the sensor chip is then coated with gold, leaving the fluid flow channel region not covered with gold. The masking material is removed, then a solution of hydrophobic molecules which have a sulfur atom attached to bind to the gold surface is added to the sensor chip, thereby coating the sensor surface with a hydrophobic molecule while leaving the sensor channel uncoated with hydrophobic molecules. The hydrophobic molecules reduce atmospheric vapor condensation on the top surface of the chip, thereby minimizing dilution of the sample stream with the liquid collected on the surface of the silicon chip. The molecules also direct the free surface flow to follow a defined path which may be more hydrophilic. Molecules such as alkanes, benzene derivatives, and other molecules such as organics may be used as hydrophobic molecules. One example is 1-hexanethiol, others will be readily apparent to those of skill in the art.

The open fluid flow channel surface is coated with a material which binds to an agent attached to a hydrophilic molecule which is added to the sensor surface. The result is to make the open fluid flow channel sensor surface hydrophilic in order to induce wetting. An example coating material may be gold. An example agent attached to the hydrophilic molecule may be sulfur. An example hydrophilic molecule is polyethylene glycol.

The hydrophilic material added to the open fluid flow channel wall surfaces also reduces adsorption of contaminants onto the fluid flow channel walls.

A nanostructured, superhydrophilic material added to the (open or closed) fluid flow channel walls to improve wettability. The resulting superhydrophilic surface is hydrophilic and causes rapid filling of the fluid flow channel volume.

Channels can be connected to create 'compartments' on the chip, each of which prevents diffusion of adsorbate from one compartment to the next. The compartments can be 5 microns wide×5 microns long×2 microns tall and can be comprised of 1 micron thick walls. The compartments can be coated with microstructured material and/or silver or gold for increased SERS response. The compartments can be wetted by adding a drop of water or silver/gold colloid to the chip which contains one or many compartments, yet the 'excess' liquid could be wiped free or otherwise removed to produce individual wetted compartments.

In one aspect, a free-surface detection device can be coupled with a commercially-available hand-held Raman spectrometer to create a field-portable rugged SERS detector.

The demonstrated method of controlled amplification of molecular recognition of airborne species by SERS probes comprises a majority of the target molecular structure, which is reported in the Raman signal. The fact that a large fraction of the analyte chemical signature is recorded is a useful aspect of the detection system of the disclosure.

In one aspect, the disclosure provides a SERS device that is a "signal-on" system in the sense that increasing analyte concentration increases the sensor response, whereas previous devices are a signal-off system in which detection is indicated by the reduction of an initially larger background signal. The signal-to-noise ratio of a signal-off system is limited by the resolution of the initial background signal. The signal-on SERS system is designed to provide high signal-to-noise ratio measurements at all analyte concentration values.

Another advantage of the Free Surface microfluidic-based sensor and system of the disclosure is that the liquid surface can be continuously refreshed. This prevents signal degradation from the proposed device due to aging effects of exposed nanoparticles. Additionally, daily maintenance and operating costs of the disclosed disclosure is nearly negligible, since the consumption rate of SERS substrate is approximately 0.1 µL/day. An estimated total power consumption of each fully operational sensor device is about 100 mW and can be less than about 100 mW.

Nanostructures (e.g., nanoparticles, spheres, cubes, cylinders, rings and the like) of the disclosure can be non-functionalized or bio-functionalized. Unlike conventional fluorescence imaging, Raman spectroscopy acquires unique signatures of chemical and biological molecules without labeling with fluorophore molecules.

A microfluidic stream of Ag colloid can be combined with a microfluidic stream of an aggregation-promoting agent such as NaCl or other ions in order to induce the charge-collapse necessary for SERS enhancement between the suspended nanoparticles. When interrogated by an appropriate SERS laser (for example a HeNe laser operating at 633 nm wavelength), the nanoparticle solution provides a SERS substrate of controllable hot-spot activity such that the aggregation is observed to increase down the length of the fluid flow channel regardless of the presence of aggregation-inducing species in the immediate atmosphere. In this embodiment, the activity of the resulting SERS substrate is controllable by attenuating the concentration and flow rate of the aggregation-inducing material into the nanoparticle stream.

SERS nanoparticles of the disclosure typically comprise a noble metal. In some embodiments, the metal is silver or gold. However, the disclosure is not limited to the use of silver or gold. Any noble, transition, alkali, alkaline, or other metal may be utilized, including, but not limited to, Pt, Ti, Cu, Ru, Rh, Pd, Co, Ni, Cr. In certain embodiments, a 1 nm layer of titanium or chromium is added to the surface of the particles prior to application of the metal (e.g., gold or silver) in order to improve the adhesion of the silver to the surface of the polymer.

In one embodiment, the disclosure provides a biocompatible metallic composite (e.g., Au/Ag/Fe/Au) nanostructure. Various polymers may be used as the template nanostructure in the generation of a nanostructure of the disclosure. For example, o-polyacrylamide and poly(vinyl chloride), poly (vinyl chloride) carboxylated, polystyrene, polypropylene and poly(vinyl chloride-co-vinyl acetate co-vinyl) alcohols, may be used.

Silver, gold and copper are useful SERS-enabling metals, less ideally indium, aluminum and platinum and even less so other metals. The nanostructured surface may be an assembly of nanoparticles. Experience teaches that the best results are obtained when the SERS-active substrate is composed of closely arrayed, interacting nanoparticles or nanostructures so constructed as to allow the analyte or a portion thereof to occupy a small crevice between particles with dimensions from 0.5 to 40 nm. The enhancement in Raman signal and therefore in analysis sensitivity brought about by placing the analyte in close proximity to the SERS-active substrate is very large (up to 14 orders in magnitude), so large at times that Raman signals arising from single analyte molecules or a small number of analyte molecules may be readily recorded. This makes SERS potentially among the most sensitive analysis techniques with molecular identification capabilities. Moreover, Raman is a vibrational spectroscopy that can provide molecular identity and quantification.

For example, strongly-interacting silver or gold nanoparticles often result when molecules, such as most analytes, replace the charged species present at the surface of stable colloidal metal particles in solution. This replacement process promotes the aggregation of the metal (e.g., silver) nanoparticles into closely packed arrays ideal for SERS, which, as a result, displays the SERS spectrum of the desired analyte or analytes that have been incorporated into the metal-nanoparticle aggregates.

In one embodiment, a suitable silver colloid solution is continuously flowed through a free-surface microfluidic device. Because the channel is open, molecular species (i.e., analytes to be detected) from a sample area enter the channel promoting nanoparticle aggregation leading to the appearance of the SERS signature of the analyte materials. At steady state and with laminar flow, the distance from the entry point of the channel is typically proportional to the exposure time of the flowing colloid solution to the atmosphere. Moreover, since a colloid flow in the system can be continuous, the SERS signal reports the continuously changing composition of the atmospheric environment probed. Further, nanoparticle aggregation is a time dependent process. Since the movement of nanoparticles down the fluid flow channel is also a function of time, the self-assembly of nanoparticles into aggregates of increasing size is related to the stream-wise distance the aggregate has moved with the flow down the fluid flow channel. The enhancement factor of the Raman scattering due to the SERS effect is likewise resolved down the length of the fluid flow channel. Since a typical nanoparticle aggregate will evolve from a single particle upon entry into the region of the fluid flow channel which is exposed to the analyte into a larger aggregate as it flows down the fluid flow channel length and is exposed to other particles with which aggregation can occur, the entire length of the channel can be interrogated by Raman spectroscopy to identify the region in which the SERS effect is greatest.

The devices, systems, methods and techniques can be used to measure any number of volatile agents in any number of industrial applications. The devices, systems and method of the disclosure offer ease of use, speed, and identification of analytes in a portable, relatively inexpensive implementation. Thus, a wide variety of analytes can be identified and analyzed by the disclosed devices, methods and systems. Detectable analyte include broad ranges of chemical classes such as organics including, for example, alkanes; alkenes; alkynes; dienes; alicyclic hydrocarbons; arenes; alcohols; ethers; ketones; aldehydes; carbonyls; carbanions; sugars; biogenic amines; thiols; polynuclear aromatics and derivatives of such organics, e.g., halide derivatives, and the like; biomolecules such as proteins, DNA, RNA, hormones, other signaling components of the endocrine and other biosystems, components of biotissues, blood, and other biofluids; isoprenes and isoprenoids; and fatty acids and derivatives. Accordingly, commercial applications include environmental toxicology and remediation, biomedicine, materials quality control, food (and beverage) and agricultural products monitoring, the presence of wine freshness or bottling, cork or barrel contamination (by contaminants such as 2,4,6-trichloroanisole (TCA) guaiacol, geosmin, 2-methylisoborneol (MIB), octen-3-ol and octen-3-onein), measuring cadaverine for rapid assessment of bacterial quality and/or food spoilage, anaesthetic detection, automobile oil, gasoline, fuel or radiator fluid monitoring, breath alcohol and drug analyzers, hazardous spill identification, explosives detection, biowarfare detection, fugitive emission identification, medical diagnostics, glucose monitoring, fish freshness, detection and classification of bacteria and microorganisms for biomedical uses and medical diagnostic uses, and the like. A wide variety of commercial applications are available including, but not limited to, heavy industrial manufacturing, ambient air monitoring, worker protection, emissions control, product quality testing, leak detection and identification, oil/gas petrochemical applications, combustible gas detection, $H_2S$ monitoring, hazardous leak detection and identification, emergency response and law enforcement applications, illegal substance detection and identification, arson investigation, enclosed space surveying, utility and power applications, emissions monitoring, transformer fault detection, food/beverage/agriculture applications, freshness detection, fruit ripening control, fermentation process monitoring and control applications, flavor composition and identification, product quality and identification, refrigerant and fumigant detection, cosmetic/perfume/fragrance formulation, product quality testing, personal identification, chemical/plastics/pharmaceutical applications, leak detection, solvent recovery effectiveness, perimeter monitoring, product quality testing, hazardous waste site applications, fugitive emission detection and identification, leak detection and identification, perimeter monitoring, transportation, hazardous spill monitoring, refueling operations, shipping container inspection, diesel/gasoline/aviation fuel identification, building/residential natural gas detection, formaldehyde detection, smoke detection, fire detection, automatic ventilation control applications (cooking, smoking, etc.), air intake monitoring, hospital/medical anesthesia and sterilization gas detection, infectious disease detection and breath applications, body fluids analysis, pharmaceutical applications, drug discovery and telesurgery. Another application for the fluidic device of the disclosure is in engine fluid monitoring (e.g., an oil/antifreeze monitor, engine diagnostics for air/fuel optimization, diesel fuel quality and the like). Volatile organic carbon measurement (VOC), fugitive gases in refineries, halitosis, soil and water contaminants, leak detection, fire safety, chemical weapons identification, use by hazardous material teams, explosive detection, breathalyzers, ethylene oxide detectors and anesthetic measurements can also be performed.

The methods and devices of the disclosure can be used for military and public safety in a variety of venues. For example, the instrument could be used in airports to screen baggage and in military environments for detection of IEDs or landmines. Large numbers of sensors could also be deployed as the front-end for a distributed network system for airborne monitoring. The microfluidic platform provided by the disclosure can be integrated with on-chip laser diodes and photo diodes to create a low-cost sensor for distributed sensing applications.

A free-surface detection system of the disclosure is attractive as detection systems of a wide variety of airborne agents, as they present a high surface area-to-volume ratio in the flow, which enables efficient absorption and subsequent detection of the absorbed species by Surface-Enhanced Raman Spectroscopy (SERS).

A method for detection of airborne agents, such as explosives, may include (but not limited to) the following objectives: (1) field portable—light weight, low power, durable, (2) high sensitivity, (3) molecular specific detection and (4) multiplexed chemical sensing. Although there are several current technologies for detecting airborne explosives, none of them meet all four of these objectives. However, the SERS-based microfluidic approach disclosed here does meet (but not limited to) these four objectives: (1) it is microfluidic-based and can be made very portable, (2) the SERS detection allows it to be highly sensitive, (3) the SERS signature allows it to be molecular specific, and (4) the system can perform multiplexed chemical sensing.

The free-surface fluidics/SERS sensor can be enhanced further by adding a 'sniffer' that directs air flow from the surrounding atmosphere towards the free surface. This enhances the exposure of sensor to the atmosphere. In addition, the sniffer can be fitted with a filter to remove particles that could potentially contaminate the sensing surface.

As stated earlier, a highly effective method for detection of airborne explosives may consist of the following objectives: (1) field portable—light weight, low power, durable, (2) high sensitivity, (3) molecular specific detection and (4) multiplexed chemical sensing. As explained below, the SERS-based Free Surface microfluidics (FSF) approach exploits physical phenomena at the micro/nanoscale to achieve these objectives.

The microfluidic architecture is useful for tracking and deterministically controlling colloidal aggregation, allowing one to optimize and control SERS 'hot spot' formation, which leads to the controlled production of very large SERS intensity enhancement (e.g., up to 14 orders of magnitude increase in signal compare to normal Raman scattering). In this system, analyte (adsorbate) molecules displace ionic species on the surface of the silver colloidal particles, thus reducing the Coulombic barrier. This promotes the sequential aggregation of nanoparticles into SERS-active dimers, trimers and larger species, which can be deterministically monitored in the microfluidic platform. Because downstream position in the microfluidic channel corresponds to a specific duration of exposure time of colloidal nanoparticles to analyte (adsorbate) molecules, the 'hot spot' formation is maximum at a particular stream-wise position, and is statistically stationary in time.

In one aspect, trace amounts of a species in the atmosphere (such as, for example, residual molecules emanating from a concealed explosive device) can be concentrated sufficiently in the probe-volume so that the ratio of nanoparticles (e.g., silver particles) to analyte molecules reaches an appropriate level. This is possible when the probe-surface to the probe-volume ratio is very large. This can be achieved by using a micro/nanofluidic system. To help gauge the possibilities, consider a 10 µm long×2 µm wide×1 µm deep fluidic channel, which is exposed to an atmosphere containing 1 ppb of a target analyte. The concentration of analyte crossing the 20 µm$^2$ surface will be approximately $10^4$ times larger than would be the case in a macroscopic system, such as a 10 cm×10 cm×1 cm dish. SERS sensing has been demonstrated at lower than nanomolar concentration.

The probe, in this case the analyte-covered silver nanoparticle system, is irreversibly altered by the analyte. Hence, continuous monitoring is possible by continuously exposing the environment being probed to fresh nanoparticles. In a macroscopic system this is expensive and wasteful. In the microfluidic system described here, a typical flow rate is 5 nL/hr. Therefore a microliter droplet of silver-nanoparticle solution provides 200 hours of continuous analysis. This allows the device to be operated inexpensively for long periods of time.

In addition to the non-functionalized nanoparticle SERS probes described above, the nanoparticle SERS probes can be functionalized (i.e. "smart SERS probes".) The term "functionalized" is meant to include structures with two or more layers of different metals, structures with functional groups attached thereto, structures that have optical properties, magnetic structures, etc.

The nanoparticles of the disclosure can optionally be functionalized by imprinting functional groups, such as antibodies, proteins, nucleic acids, and the like. Such nanostructures are particularly useful for molecular diagnostics. For example, to prolong or target analyte interaction with the noble metal nanoparticle surface, a binding agent/targeting domain is used to promote interaction of a nanostructure with a desired target. An alkanethiol, such as 1-decanethiol, can be used to form the capture layer on the noble metal (Blanco Gomis et al., J. Anal. Chim. Acta 436:173, 2001; Yang et al., Anal. Chem. 34:1326, 1995). Other exemplary capture molecules include longer-chained alkanethiols, cyclohexyl mercaptan, glucosamine, boronic acid and mercapto carboxylic acids (e.g., 11-mercaptoundecanoic acid).

Alternatively, a self-assembled monolayer (SAM) is formed on the nanostructure surface to concentrate the analyte of interest near the surface of the nanostructure. Exemplary SAMs include, but are not limited to, 4-aminothiophenol, L-cystein, 3-mercaptopropionicacid, 11-mercaptoundecanoic acid, 1-hexanethiol, 1-octanethiol, 1-DT, 1-hexadecanethiol, poly-DL-lysine, 3-mercapto-1-propanesufonic acid, benzenethiol, and cyclohexylmercaptan. Typically the SAM is comprised of straight chain alkanethiols.

In other embodiments, nanostructures of the disclosure are coated to inhibit the accumulation of biological material (e.g., proteinaceous agents) on the nanostructure's surface. In some embodiments, polyethyleneglycol (PEG) is immobilized on nanostructure surfaces to prevent nonspecific interactions. In some embodiments, silica sensor surfaces not coated with silver are PEGylated with silane terminated monomethoxyPEG and silver coated nanoparticle surfaces are coated with oligoethyleneglycol terminated alkanethiols.

Attached functional groups can comprise components for specific but reversible or irreversible, interactions with a specific analyte (e.g., can be labeled for site/molecule directed interactions). For example, a surface bound functional group (e.g., a targeting ligand) can be attached to a nanostructure of the disclosure. For example, a chemical molecule can be immobilized on the surfaces of a nanostructure of the disclosure. The disclosure demonstrates that a self-assembled monolayer of 3-mercaptopropyltrimethoxysilane (MTMO), a thiol-group containing molecule, can be attached to the surface of the nanostructure through Au sulfide bonds by spreading and drying a droplet of 1 lM MTMO in anhydrous ethanol solution.

A targeting ligand can include a receptor bound to the surface of a nanoparticle that interacts reversibly or irreversibly with a specific analyte. Typically, the interaction of the targeting ligand and the analyte lasts sufficiently long for detection of the analyte by SERS.

Examples of functional groups (e.g., targeting ligands) include antigen-antibody pairs, receptor-ligand pairs, and carbohydrates and their binding partners. The binding ligand may be nucleic acid, when nucleic acid binding proteins are the targets. The nucleic acid may also bind to another nucleic acid. As will be appreciated by those in the art, the composition of the binding ligand will depend on the composition of the target analyte. Binding ligands to a wide variety of analytes are known or can be readily identified using known techniques.

For example, when the analyte is a single-stranded nucleic acid, the binding/targeting ligand is generally a substantially complementary nucleic acid. Similarly the analyte may be a nucleic acid binding protein and the capture binding ligand is either a single-stranded or double-stranded nucleic acid; alternatively, the binding ligand may be a nucleic acid binding protein when the analyte is a single or double-stranded nucleic acid. When the analyte is a protein, the binding ligands include proteins or small molecules. For example, when the analyte is an enzyme, suitable binding ligands include substrates, inhibitors, and other proteins that bind the enzyme, i.e. components of a multienzyme (or protein) complex. As will be appreciated by those in the art, any two molecules that will associate, may be used, either as the analyte or the functional group (e.g., targeting/binding ligand). Suitable analyte/binding ligand pairs include, but are not limited to, antibodies/antigens, receptors/ligand, proteins/nucleic acids; nucleic acids/nucleic acids, enzymes/substrates and/or inhibitors, carbohydrates (including glycoproteins and glycolipids)/lectins, carbohydrates and other binding partners, proteins/proteins; and protein/small molecules. In one embodiment, the binding ligands are portions (e.g., the extracellular portions) of cell surface receptors.

A sufficiently large free surface is useful for carrying out high sensitivity detection of explosives or other analyte molecules. The free surface architecture allows one to maximize the surface to volume ratio. For example, the surface to volume ratio produced by the free-surface fluidic channel is nearly 20 times greater than the surface to volume ratio of a 100 µm diameter droplet. Moreover, the system must incorporate fluid flow so as to satisfy continuous analysis. Rapid flow in macroscopic open channels is unstable since the surface tension forces cannot overcome the fluid's tendency to leave the channel. In a microfluidic channel, the surface forces trap the liquid to the body of the channel.

As mentioned above, the detection devices of the disclosure are capable of multi-channel analysis and scaling. The small length scales associated with microfluidics facilitates fabrication of multi-channel devices, whereby each fluid flow channel is sensitive to one, or a class of target analytes. This can be achieved by functionalizing the nanoparticles (e.g., a metallic nanoparticle) with species that have specific molecular recognition. As described elsewhere herein such nanoparticles can be further functionalized. For example, thiol- or amine-functionalized oligonucleotides bind to the silver surface at the sulfur or amine end, exposing the other end to analyte. A complementary oligonucleotide will bind specifically a particular DNA sequence, which is detectable as a change in the SERS spectrum. One can envision a device comprising several side-by-side channels, each fed from a reservoir in which the metallic (e.g., silver or gold) nanoparticles are appropriately functionalized to recognize a specific molecule or class of molecules. The SERS analysis can be carried out sequentially on the channels under digital control, thereby providing a multiplex detector whose overall utility would be to reduce the probability of false positives and to provide "background" controls by, for example, providing a control spectrum with unfunctionalized nanoparticles.

Multiple microfluidic channels provide flexible designs for 'lab on a chip' concepts. For example, microfluidic channels can be used to provide controlled dilution of analyte. The diluted analyte can then be introduced to nano-particle flow and SERS detection can be performed. The SERS intensity can then be compared to the degree of dilution, to facilitate the deduction of initial analyte concentration.

The relative concentration of two or more analytes can be deduced by decomposing the composite SERS spectrum into the SERS spectrum of each individual analyte. Assuming 'hot spot' aggregation is consistent between analytes, the relative intensity of each individual SERS spectrum can be used to estimate the relative concentrations of each analyte.

A SERS-active film can be self assembled using the free-surface fluidic architecture. Colloidal solution (e.g., silver or gold nanoparticles) can be flowed into the fluid flow channel. The liquid can be evaporated leaving the nanoparticles deposited on the fluid flow channel surface, thereby creating a SERS-active film. The properties of the film can, in principle, be controlled by: initial colloid concentration, the specific temperature profile used to heat the chip to drive the evaporation of the aqueous phase, and the fluid velocity. After exposure, the film can be removed by flowing liquid into the fluid flow channel and allowing the nanoparticles to be re-absorbed into the flowing liquid. A new SERS-active film can then be re-deposited onto the fluid flow channel surface, by flowing in colloidal solution, and re-evaporating the liquid.

Various embodiments of the disclosure include, for example, a Free Surface Fluidics (FSF) SERS system; a Membrane Confined Fluidics (MCF); an Enclosed Fluid flow channel Fluidics (EMF); a Thin film Fluidics (TFF); and a Digital Microfluidics (DMF).

Figure 9:
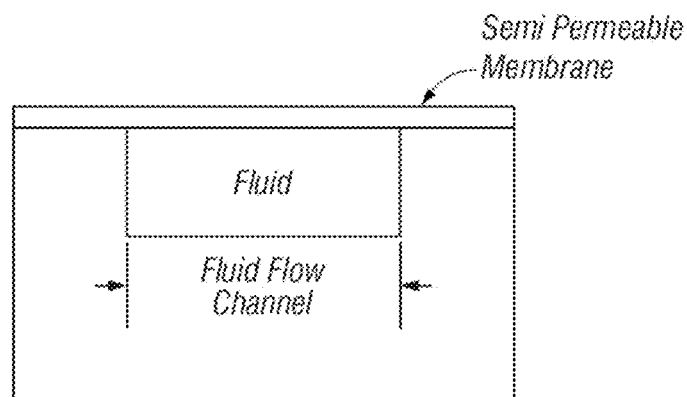

In one embodiment a Free-Surface Fluidic architecture described herein as an exemplary embodiment is used. In another embodiment, a Membrane Confined Fluidics (MCF) SERS system is provided. This embodiment is similar to the Free-Surface Fluidic architecture, except the free surface is replaced by a thin semi-permeable membrane (see, e.g., FIG. 9). The thin membrane confines the flowing fluid, but allows small analytes to penetrate and diffuse into the fluid. Some advantages of the membrane include, for example: (1) the fluid is more stable than the free surface, (2) large contaminants (such as dust) in the air are filtered by the membrane, keeping the liquid uncontaminated, (3) the device may have a longer shelf life, and (4) there is less requirements on temperature to prevent evaporation.

Figure 10:
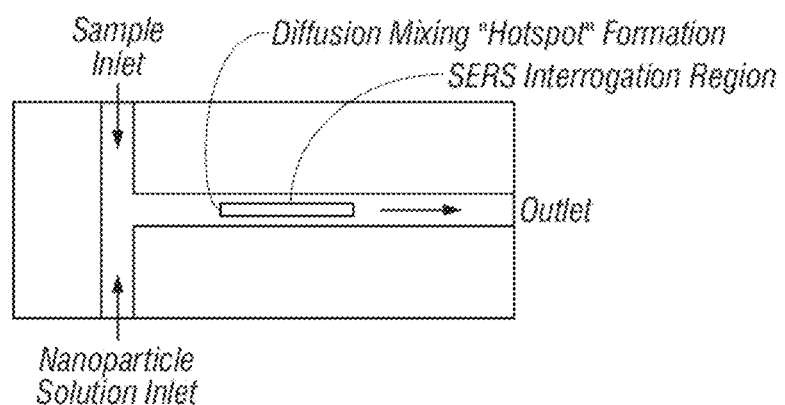

In yet another aspect, an Enclosed Fluid flow channel Fluidics (EMF) is provided. In this embodiment, the sample is introduced to the nanoparticle solution inside an enclosed microfluidic channel. For example, the two fluid streams can be introduced through a T-junction (as shown in FIG. 10). The laminar nature of microfluidics will create a stable interface between the two fluid streams. Diffusion of analyte across the interface will create controlled aggregation of the SERS nanoparticles, thereby creating a SERS 'hot spot' at deterministically controlled regions in the fluid flow channel. Some advantages of the enclosed fluid flow channel embodiment are: (1) the fluids are fully contained by the fluid flow channel, (2) the fluids are more easily controlled, and (3) it is easier to keep contaminants out of the flowing channels.

Figure 11:
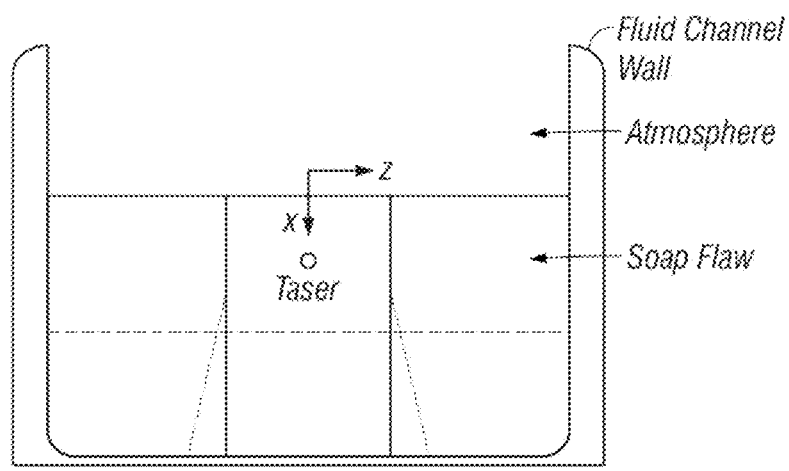
Figure 12:
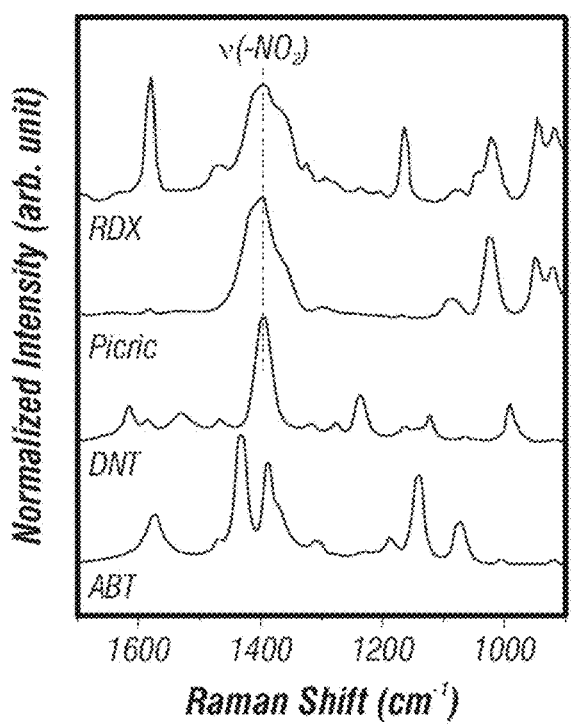
Figure 13:
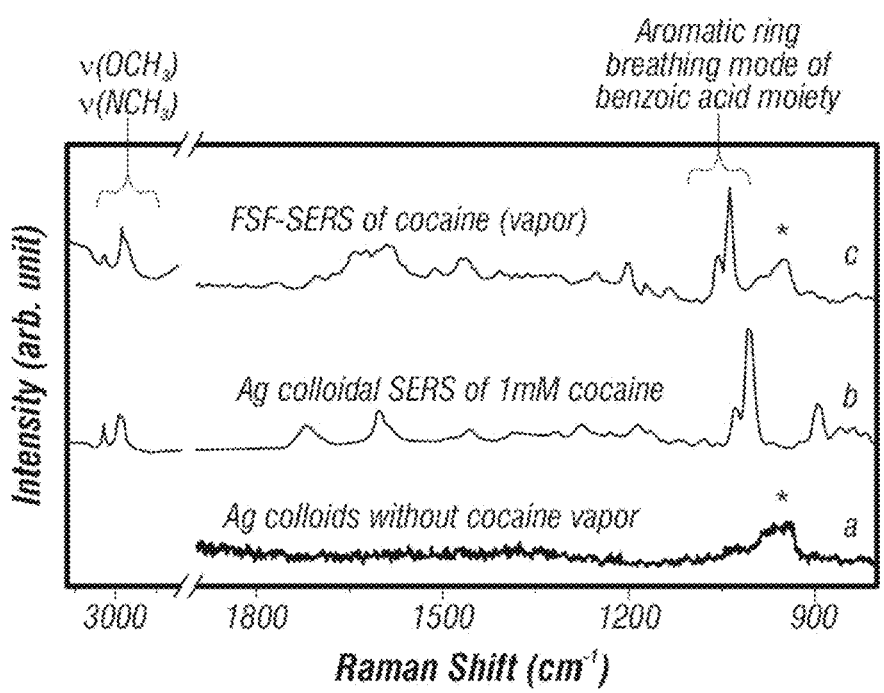
Figure 14:
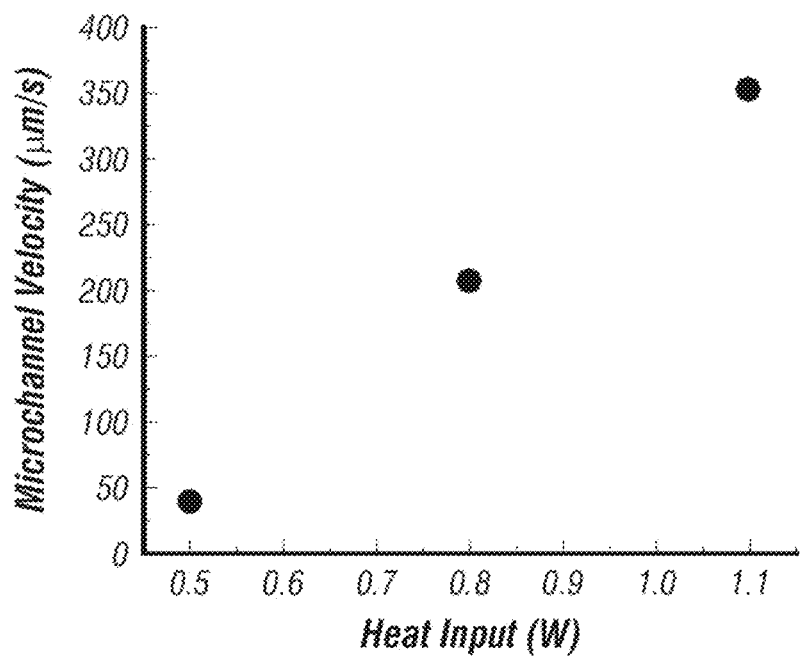
Figure 15:
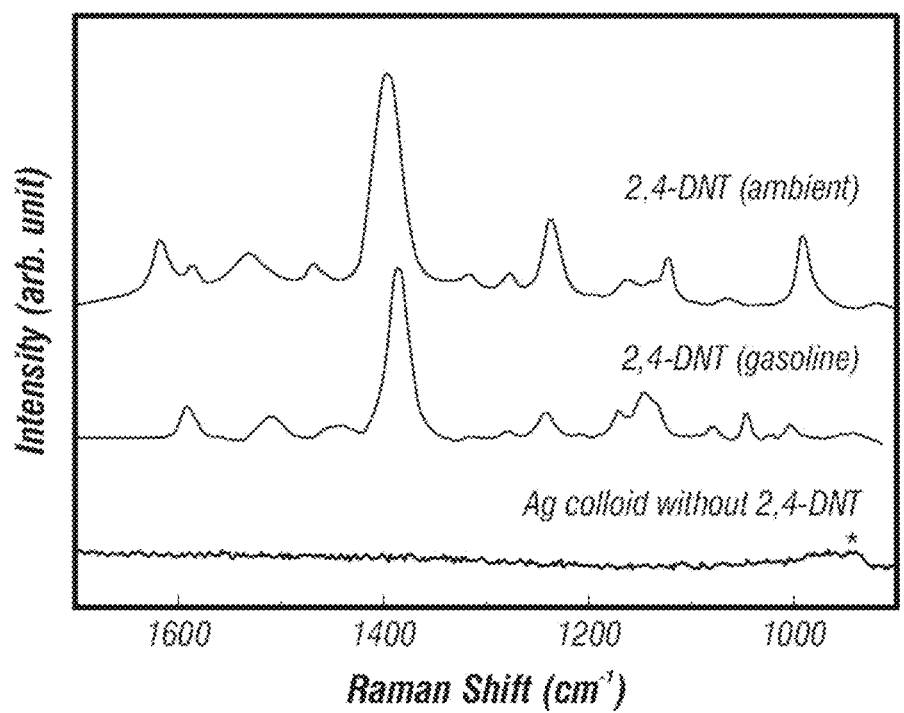

In yet a further embodiment, a Thin Film Fluidics (TFF) system is provided. In this embodiment, a thin film (similar to a suspended soap film) containing nanoparticles is exposed to the atmosphere. Once the particles are exposed to analyte, they aggregate. This embodiment is similar to the FSF embodiment, except the thin film can be exposed on two sides, instead of just one side as depicted in the FSF embodiment. In addition, if a surfactant is added to the fluid, the thin film can be made of ~1 cm in width and length and an order ~1 µm in thickness. Thin film flows have been investigated by Berg et al. (2005). FIG. 11 shows a typical suspended soap film. It is important to note that a wide variety of fluids, which may or may not contain surfactants, may be used to create a thin film fluidic.

A Digital Microfluidics (DMF) system is also provided by the disclosure. Digital microfluidics is an area of microfluidics where droplets of one immiscible fluid are injected into another immiscible fluid. The results are discreet droplets that are ~nL in volume. For example, three aqueous solutions are injected into an oil flow through the fluid flow channel. One could imagine that the SERS nanoparticles and sample (analyte) are mixed in a controlled fashion in the discrete droplets.

Analytes that can be detected or measured by the compositions and methods of the disclosure include any molecule or atom or molecular complex suitable for detection by the nanostructures of the disclosure. Examples of such analytes include, but are not limited to, biomolecules such as proteins, peptides, polynucleotides, lipids and the like, glucose, ascorbate, lactic acid, urea, pesticides, chemical warfare agents, pollutants, and explosives.

In some embodiments, the disclosure provides kits and systems for use in monitoring the level of an analyte in a sample or subject. In some embodiments, the kits are for home use by a subject to assist in identifying an analyte, disease or disorder or to monitor a biological condition.

The disclosure has use in the detection of analytes in the environment, including explosive and biological agents. Accordingly, the disclosure is useful in Homeland Security and the military for detection of analytes. In one embodiment, the disclosure provides kits for monitoring military personnel in a war situation where they may be exposed to toxins.

As used herein, the term "sample" is used in its broadest sense. For example, a sample can comprise a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. The nanostructures can be used, for example, in bodily fluids in vivo or in vitro. Such bodily fluids include, but are not limited to, blood, serum, lymph, cerebral spinal fluid, aqueous humor, interstitial fluid, and urine.

Commercial applications of the FSF detection device, methods and system of the disclosure include environmental toxicology, materials quality control, food and agricultural products monitoring, anesthetic detection, automobile oil or radiator fluid monitoring, hazardous spill identification, medical diagnostics, detection and classification of bacteria and microorganisms both in vitro and in vivo for biomedical uses and medical diagnostic uses, infectious disease detection, body fluids analysis, drug discovery, telesurgery, illegal substance detection and identification, and the like.

The working examples below are provided to illustrate, not limit, the disclosure. Various parameters of the scientific methods employed in these examples are described in detail below and provide guidance for practicing the disclosure in general.

EXAMPLES

Various device designs are shown schematically in FIG. 1A-3B. A silver solution is pumped through an enclosed 30 μm deep×15 μm wide fluid reservoir into a shallow microchannel that is 1.5 μm deep×15 μm wide. The relatively large depth of the upstream fluid reservoir (30 μm) reduces contamination upstream of the microchannel, allowing temporally-resolved exposure measurements to be carried out. The resulting velocity is 60 μm/s. The silver solution comprises 35-40 nm diameter silver nanoparticles at a concentration of $10^{-9}$ M. The velocity in the channel is driven by surface tension forces.

A PID temperature controller was used to maintain the solution temperature at the dew point to control/minimize evaporative solvent loss at the free surface. Raman measurements were carried out at various spots along the channel. The 1.5 μm deep microchannel drains into a 30 μm deep×15 μm wide enclosed fluid reservoir. The Laplace pressure at the free-surface interface is controlled throughout the microchannel system by regulating the volume of the fluid reservoirs. The resulting pressure gradient drives the free-surface flow and allows the microchannel flow velocity to be precisely controlled.

Gas-phase sensing performance was demonstrated by establishing a low partial pressure of 4-aminobenzenethiol (4-ABT, MW=125 g/mol) in the vicinity of the microchannel at room temperature. A small pellet of 4-ABT and the microchannel were housed within a sealed box (10 cm diameter×0.6 cm tall). The solid sample was placed approximately 3 cm from the open sol flow and allowed to equilibrate for 15 minutes before SERS measurements were performed. The gas-phase concentration of 4-ABT in the containment box was estimated to be ~300 μM.

A focused λ=514.5 nm laser (SpectraPhysics 164, continuous wave) beam (~1 μm diameter) was used as Raman excitation source. The laser was scanned in the streamwise direction at 10 μm steps along the midline of the 1.5 μm deep open microchannel. Light was collected with a 50× objective and was analyzed with a confocal Raman spectroscopy system (LabRam microRaman system, Jobin-Yvon/ISA, equipped with a thermoelectrically cooled CCD detector). Each spectrum was collected in 1 s with 50 mW of laser power. The t exposure time of the solution to the vapor, $t_e$, is given approximately by $t_e=x_e/v_c$ where $x_e$ is the streamwise solution travel distance during exposure and $v_c$ is the liquid velocity near the free surface. At constant flow the distance from $x_e=0$ to the interrogation position along the channel is approximately proportional to the substrate exposure time to the analyte. This allows the SERS signal from SERS-active nanoparticle aggregates to be continuously monitored as it evolves following exposure to the analyte.

Figure 4:
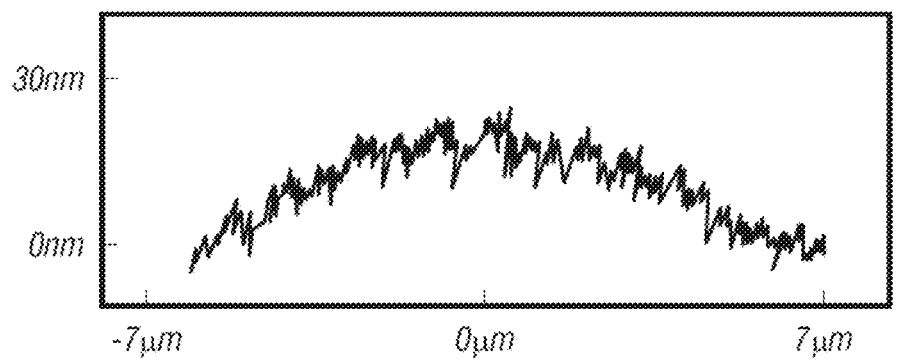
Figure 5:
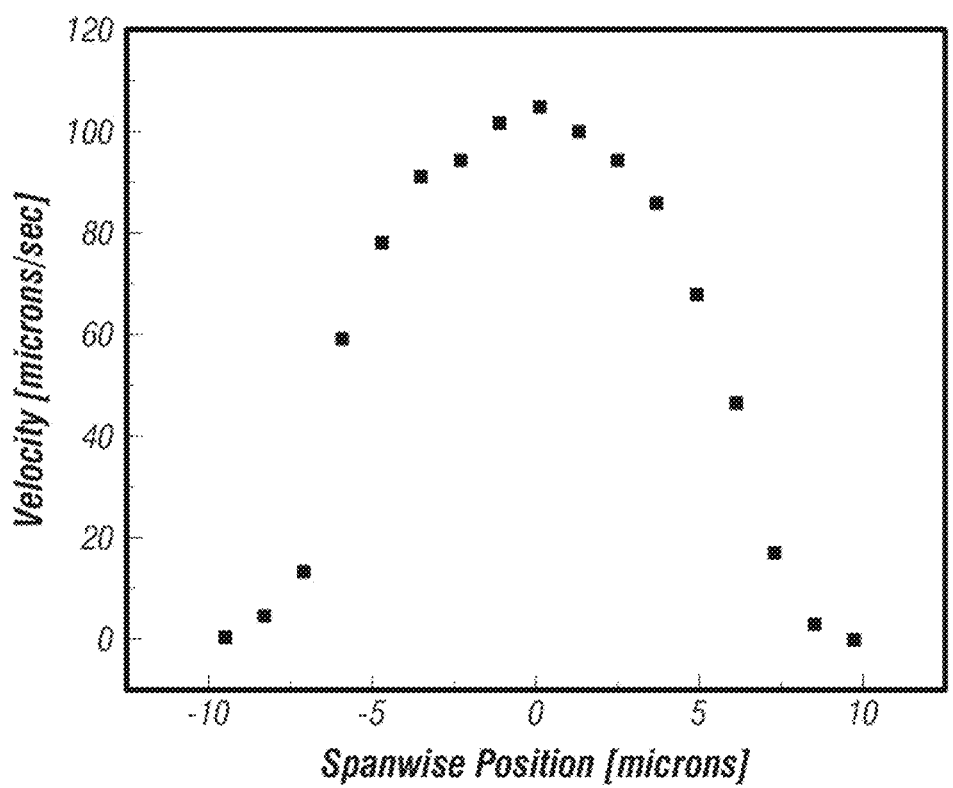

An experiment was performed to measure the curvature of a free surface area using confocal microscopy with ~10 nm resolution in the vertical direction. This gives an estimate of the local channel pressure. A typical free surface profile is shown in FIG. 4, where the radius is ~500 μm. This is sufficient to drive a 60 μm/s flow through the free-surface interaction channel. For example, pressure-driven flow in this channel has been measured using micron Particle Image Velocimetry (micro-PIV). A type of flow-tracing particle (termed Quantum Nanosphere) were used to measure fluid velocity in sub-micron channels. In one instance, the velocimetry results indicate a ~0.1 mm/s flow with a peaked velocity profile (see FIG. 5). Other experiments have established that liquid velocities ~1 mm/sec can be established in open channels ~1 μm deep.

Figure 7:
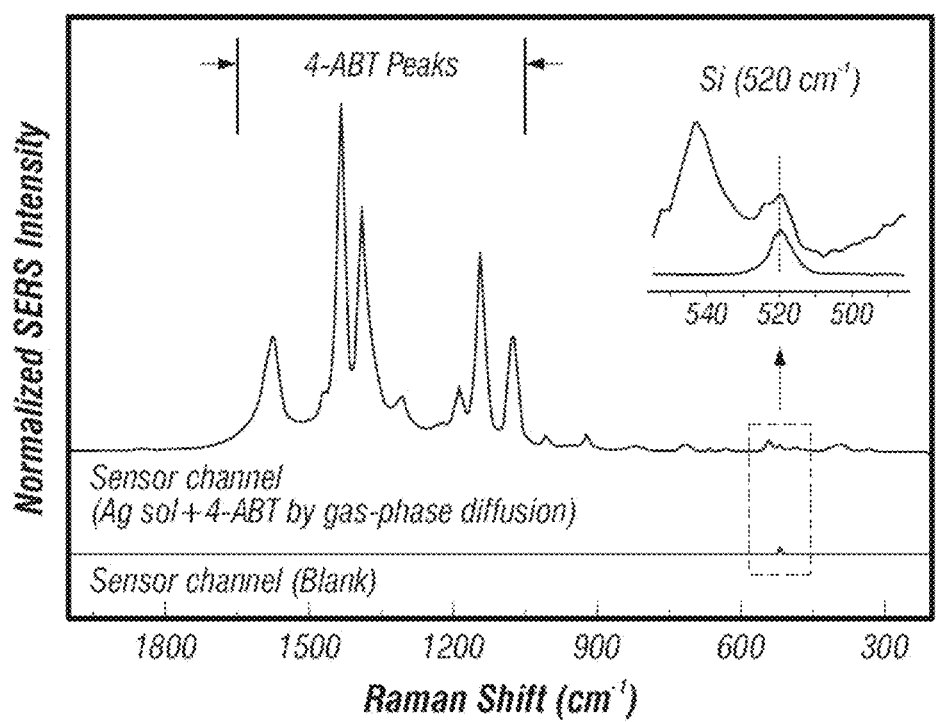

An experiment was conducted to demonstrate the SERS-based microfluidic system for high sensitivity detection of airborne explosives. Gas-phase sensing was tested by establishing a low partial pressure of 4-aminobenzenethiol (4-ABT) (a molecule similar in structure to TNT) in the vicinity of the fluid flow channel by placing a solid sample of the 4-ABT approximately 3 cm from the open solution flow within a containment box (10 cm diameter×0.6 cm tall) which helped collect the 4-ABT vapor. The central portion of the flowing colloidal solution (with a cross-section approximately 1 μm diameter by 1.5 μm deep) was monitored by confocal Raman spectroscopy. The 50 mW continuous wave 514.5 nm (SpectraPhysics 164) laser was focused through a 50× lens for 1 second. A typical Raman spectrum of 4-ABT is shown in FIG. 7. The exposure time of Ag-colloid to 4-ABT increases linearly with position down the fluid flow channel since the flow velocity is steady and maps to fluid flow channel position as $t=x_e/v_c$, where t is solution exposure time to the gaseous species, $x_e$ is the stream-wise solution travel distance since exposure, and vc is the average colloid flow velocity in the fluid flow channel. The flow adds another degree of freedom to SERS analysis whereby the distance from $x_e=0$ to the interrogation position corresponds to substrate exposure time to analyte.

In the streamwise direction of the flow, nanoparticle transport was dominated by convection since the associated Peclet number is $Pe_L \equiv v_c L/D = 1 \times 10^3$, where $v_c=60$ μm/s was the average flow velocity, L=200 μm is a characteristic length scale in the streamwise direction of the microchannel flow, and D=$1.13 \times 10^{-11}$ m$^2$/s is the nanoparticle diffusivity. The streamwise Peclet number also suggests that in the $x_e<0$ region thermal diffusion is insufficient to cause the solution to be exposed to the analyte. Because in these specific examples the system was designed such that chemical gradients in the depthwise direction of the flow would not affect aggregation dynamics, the nanoparticle distribution was nearly constant in the depthwise direction, h, of the microchannel flow. The ratio of the diffusion time scale in the depthwise direction to the advection time scale is $(v_c L/D)*(h/L)^2=3\times10^{-2}$, where $h=1$ µm is a characteristic length scale in the depthwise direction. In addition, the 4-ABT concentration was nearly constant in the depthwise direction of the microchannel flow since $(v_c L/D)*(h/L)^2=3\times10^{-3}$, where $D=1\times10^{-10}$ m$^2$/s is the diffusivity of 4-ABT.

Figure 8:
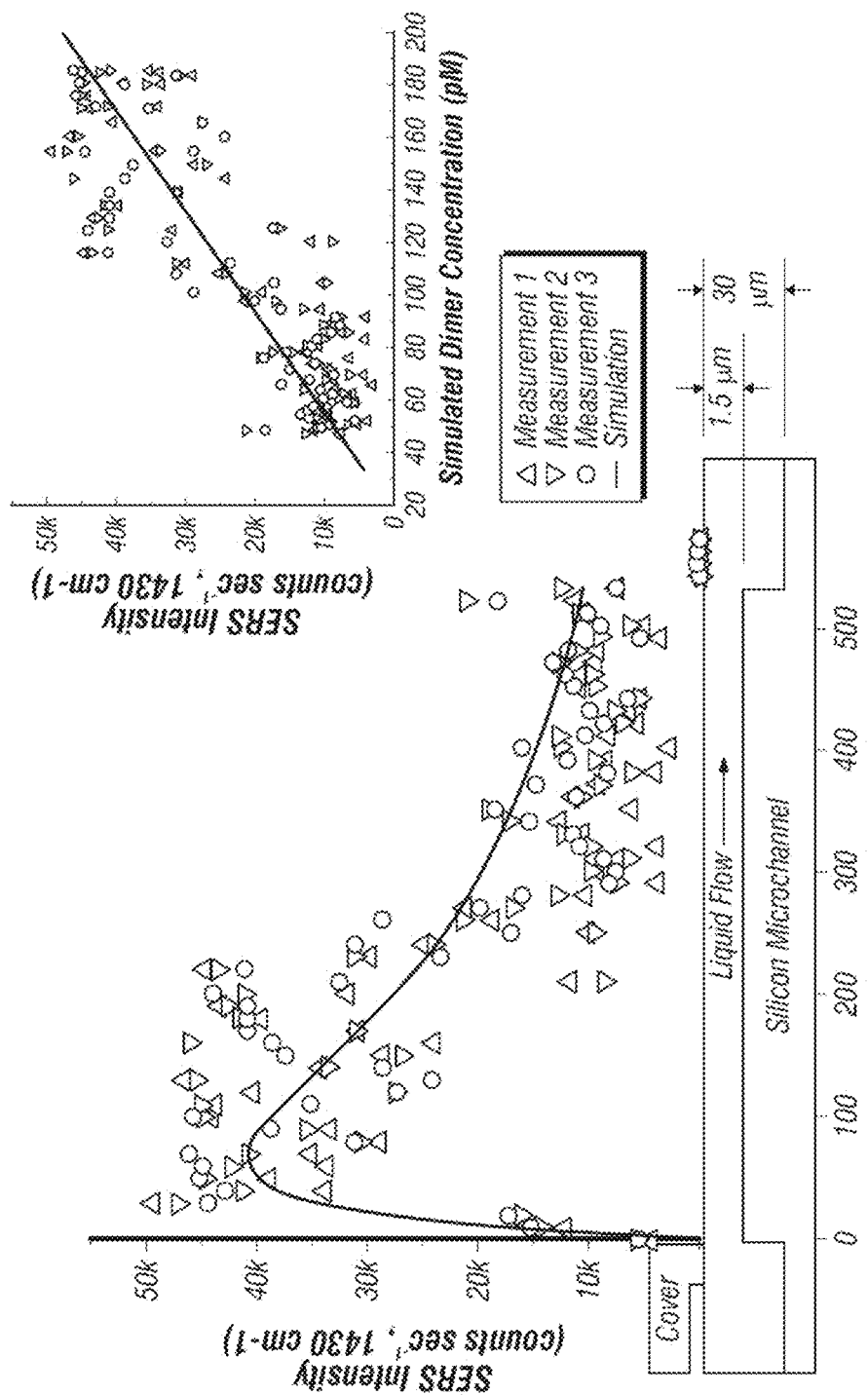

The SERS intensity of the 1435 cm$^{-1}$ Raman band of the 4-ABT as a function of position along the fluid flow channel is shown by symbols in FIG. 8. The microflow was covered in the region $x_e<0$ to prevent premature solution exposure to gas-phase 4-ABT. It was uncovered in the region $x_e>0$, allowing nanoparticle exposure to 4-ABT at a gaseous concentration estimated to be ~300 µM. Nanoparticle transport was dominated by convection since the microflow Peclet number was $P_e=vc\, L/D=5.4\times10^3$, where L is a typical length scale, and D is the nanoparticle diffusivity. Three independent SERS intensity measurements were taken stepwise at 10 µm intervals between fluid flow channel positions $x_e=0$ µm and $x_e=570$ µm. Diffusion-driven exposure of the flowing solution to 4-ABT eliminated the need for manual sample injection, producing an autonomous environmental chemical sensor.

The SERS signal intensity is greatly increased in the 1.5 µm deep portion of the fluid flow channel. In this region, the fluid flow channel depth is matched to the penetration depth of the SERS excitation laser and the collection optics. Furthermore, confinement of analyte to the thin liquid flow eliminates signal losses from diffusion of analyte away from the interrogation region. The sensor signal diminishes in the 30 µm deep downstream fluid reservoir at values of $x_e>530$ µm. In this region, a slower bulk flow rate results from a twenty-fold increase in depth, causing the rapid formation of larger and therefore less SERS-active nanoparticle clusters.

Nanoparticles are known to aggregate when exposed to species such as the 4-ABT used in this study. FIG. 8 shows a maximal SERS response between distances of $x_e$~50 µm to $x_e$~150 µm. The average velocity was vc=60 µm/s, corresponding to solution exposure times of 1-3 s to generate the maximum SERS signal intensity.

Colloidal nanoparticle aggregation kinetics have been studied at static liquid interfaces as a function of colloid hydrophobicity. Since the suspended metal clusters are hydrophilic, the capillary forces at the free surface can be assumed to negligibly affect aggregation dynamics. The colloid aggregation is also assumed to be limited by diffusion of nanoparticle aggregates.

FIG. 8 shows an example of the shape of a typical SERS intensity-vs-streamwise position curve. This example curve corresponds to dimer concentration, and can be explained by nanoparticle aggregation kinetics. Single Ag particle-adsorbate monomers are ~4 orders of magnitude less SERS active than aggregate dimers. Similarly, SERS response of aggregate assemblies of more than two nanoparticles normally have SERS cross-sections that are somewhat smaller (on a per adsorbed molecule basis) than that of the dimer.

The free-surface colloid aggregation kinetics and the corresponding SERS response were simulated with Comsol Multiphysics 3.3. Diffusion constants for one- to four-nanoparticle aggregates were calculated from the Stokes-Einstein equation by using the geometric mean aggregate diameter. Since the diffusivity decreases for increasing aggregate size, the simulated aggregation kinetics decreases with increased aggregate volume. The SERS intensity is assumed to be proportional to dimer concentration. Therefore, the numerically-simulated dimer concentration is shown by the solid line in FIG. 8. The shape of the dimer-concentration curve corresponds closely with the experimentally-measured SERS intensity. This suggests that colloidal aggregation kinetics is responsible for the observed peak in SERS signal intensity, for this example.

Assuming 190 µM nanoparticle concentration is being advected across a 1 µm$^3$ SERS interrogation volume with a velocity of $v_c=60$ µm/s, approximately six dimers are observed during the 1 s duration interrogation time. The number of dimers observed at any one interrogation time is sufficiently low, such that the small-number statistics can provide useful information regarding the aggregation process.

The 1.5 µm deep microchannel interrogation region is matched to the penetration depth of the SERS excitation laser and the Raman signal collection optics. The confinement of analyte and SERS-active species to the laser penetration depth eliminates signal losses due to diffusion away from the SERS interrogation system.

The sensor signal diminishes in the 30 µm deep downstream fluid reservoir at values of $x_e>530$ µm. In this region, the twenty-fold increase in depth allows the SERS active species to diffuse away from the SERS laser penetration region, resulting in the detection of fewer nanoparticle clusters.

The simulation model accurately preserves the mobility ratio of the lower-order aggregate species and omits the contributions of larger aggregates that, at any rate, contribute less efficiently to Raman scattering (see, e.g., FIG. 8 (solid line)). The correspondence between the calculated and observed SERS intensity profile as a function of streamwise position falls within the scatter of the experimental data.

The SERS cross-section of the 4-ABT molecules, that is, the ratio of SERS response per 4-ABT molecule in solution, was estimated by assuming that one analyte molecule was present and reporting the SERS response per nanoparticle dimer. Comparing the measured SERS response with the simulated concentration of nanoparticle dimers along the microchannel (FIG. 8, inset) produces a proportional relationship (with a correlation coefficient $R^2=0.78$). This suggests that the SERS cross-section is approximately constant along the entire length of the microchannel: prior to, at, and subsequent to the SERS maximum.

In these examples, the maximum simulated concentration of nanoparticle dimers is 190 pM. This concentration indicates that, on average, approximately 6 dimers were interrogated during the 1 s Raman signal accumulation period in the ~1.2 µm$^3$ focal volume. The scatter in the observed SERS intensity reported in FIG. 8 is, therefore not noise but a function of the small-number statistics of the particles crossing into the laser beam.

Aggregation can occur (but not limited to) either as a result of the nanoparticle-linking capabilities of the analyte through intrinsic functionalities such as thiolate or amine groups, or through its ability to reduce the Coulomb barrier to colloid aggregation, as was the case in this example. Accordingly, the range of molecules for which it will be sensitive is very large and embraces many classes of compounds (most explosives, for example).

A number of embodiments have been described. Nevertheless, it will be understood that various modifications may be made without departing from the spirit and scope of the description. Accordingly, other embodiments are within the scope of the following claims.

What is claimed is:
1. A free-surface detection device comprising:
a substrate;
a fluid flow channel having a first end and a second end located in or on the substrate;

at least one free-surface interface region located between the first end and the second end, wherein the free-surface interface region is open on at least one side to atmospheric air comprising an analyte;

at least one temperature control element located in the at least one free-surface interface region; and at least one controller in electrical and/or thermal communication with the at least one temperature control element to provide a controlled local evaporation rate, wherein the analyte is concentrated in the fluid flow channel due to said controlled evaporation rate.

2. The device of claim 1, further comprising at least one valve upstream or downstream of the at least one temperature control element in the fluid flow channel.

3. The device of claim 1, wherein the at least one free-surface region is in the fluid flow channel and wherein the at least one free-surface region comprises at least one wall.

4. The device of claim 3, wherein a surface chemistry of the at least one wall comprises a modification to control fluid flow.

5. The device of claim 4, wherein the modification comprises a change in hydrophobicity and/or hydrophilicity along the at least one wall's surface.

6. The device of claim 1, further comprising:

at least one excitation area, wherein electromagnetic energy excites a SERS probe in a fluid in the fluid flow channel;

at least one detection area for detecting emitted spectra; and at least one detector in optical communication with the at least one detection area.

7. The device of claim 6, wherein the at least one detector detects the presence of one or more analytes absorbed in a fluid in the fluid flow channel by a technique selected from the group consisting of Raman spectroscopy or surface enhanced Raman scattering ("SERS") measurements of a probe that is contained in the fluid; electrochemical analysis techniques; fluorescent chemical marker techniques; fluorescence quenching; redox-labeled nucleic acid binding techniques; X-Ray absorption techniques; IR, visible, and UV electromagnetic radiation absorption techniques; mass spectroscopy techniques; liquid chromatography techniques; flame ionization analysis techniques; DNA melting point techniques; and titration analysis techniques.

8. The device of claim 7, wherein the fluid comprises one or more nanoparticles.

9. The device of claim 8, wherein the one or more nanoparticles are functionalized.

10. A free-surface detection device comprising:

a fluid flow channel having a first end and a second end;

a free-surface interface region located between the first end and the second end, wherein the free-surface interface region is open to atmospheric air comprising nanoparticle colloid;

wherein said fluid flow channel further comprises a temperature control element linked to a controller for controlling the local evaporation rate; and wherein nanoparticle colloid concentration is controlled within the fluid flow channel due to said controlled local evaporation rate.

11. The device of claim 10, wherein said nanoparticle colloid aggregates due to controlled nanoparticle concentration.

* * * * *